US010566121B2

(12) United States Patent
Radovinsky et al.

(10) Patent No.: US 10,566,121 B2
(45) Date of Patent: Feb. 18, 2020

(54) IRONLESS, ACTIVELY-SHIELDED, VARIABLE FIELD MAGNET FOR MEDICAL GANTRIES

(71) Applicants: Alexey Radovinsky, Cambridge, MA (US); Leslie Bromberg, Sharon, MA (US); Joseph Minervini, Still River, MA (US); Philip Michael, Cambridge, MA (US); Emma Pearson, Schaerbeek (BE); Eric Forton, Nil-Pierreux (BE)

(72) Inventors: Alexey Radovinsky, Cambridge, MA (US); Leslie Bromberg, Sharon, MA (US); Joseph Minervini, Still River, MA (US); Philip Michael, Cambridge, MA (US); Emma Pearson, Schaerbeek (BE); Eric Forton, Nil-Pierreux (BE)

(73) Assignees: Ion Beam Applications S.A., Louvain-la-Neuve (BE); Massachusetts Institute of Technology, Cambridge, MA (US)

( * ) Notice: Subject to any disclaimer, the term of this patent is extended or adjusted under 35 U.S.C. 154(b) by 78 days.

(21) Appl. No.: 15/776,405

(22) PCT Filed: Nov. 16, 2016

(86) PCT No.: PCT/US2016/062312
§ 371 (c)(1),
(2) Date: May 15, 2018

(87) PCT Pub. No.: WO2017/087541
PCT Pub. Date: May 26, 2017

(65) Prior Publication Data
US 2018/0330857 A1 Nov. 15, 2018

Related U.S. Application Data

(60) Provisional application No. 62/256,006, filed on Nov. 16, 2015.

(51) Int. Cl.
*H05H 7/04* (2006.01)
*H01F 6/06* (2006.01)
*A61N 5/10* (2006.01)

(52) U.S. Cl.
CPC ............... *H01F 6/06* (2013.01); *H05H 7/04* (2013.01); *A61N 5/10* (2013.01); *H05H 2007/045* (2013.01)

(58) Field of Classification Search
CPC ...... H05H 7/00; H05H 2007/002; H05H 7/04; H05H 2007/045; H05H 2007/046; H05H 2007/048; H05H 13/005; H05H 13/02
See application file for complete search history.

(56) References Cited

U.S. PATENT DOCUMENTS

| 3,084,249 A | 4/1963 | Enge |
|---|---|---|
| 5,610,568 A | 3/1997 | Marroux |

(Continued)

FOREIGN PATENT DOCUMENTS

| WO | WO-2012/150448 | 11/2012 |
|---|---|---|
| WO | WO-2014/207130 | 12/2014 |

OTHER PUBLICATIONS

International Search Report and Written Opinion, dated Feb. 1, 2017, in corresponding International Application No. PCT/US2016/062312 (8 pages).

(Continued)

*Primary Examiner* — Ramon M Barrera
(74) *Attorney, Agent, or Firm* — Finnegan, Henderson, Farabow, Garrett & Dunner LLP

(57) ABSTRACT

A magnet for transporting a particle beam in a target magnet field may include a first set of coils and a second set of coils. According to some aspects, the first and second set of coils may be configured to generate a combined desired magnetic field within the bore and may be configured to generate a (Continued)

combined magnetic field weaker than the desired magnetic field outside the bore.

25 Claims, 15 Drawing Sheets

(56) References Cited

U.S. PATENT DOCUMENTS

| | | | |
|---|---|---|---|
| 5,978,694 | A | 11/1999 | Rapoport |
| 6,921,042 | B1 | 7/2005 | Goodzeit et al. |
| 7,701,677 | B2 | 4/2010 | Schultz et al. |
| 7,872,562 | B2 | 1/2011 | Meinke et al. |
| 7,889,042 | B2 | 2/2011 | Meinke |
| 8,107,211 | B2 | 1/2012 | Meinke et al. |
| 8,424,193 | B2 | 4/2013 | Meinke |
| 9,349,513 | B2 | 5/2016 | Meinke |
| 2013/0229086 | A1 | 9/2013 | Meinke |
| 2014/0087953 | A1 | 3/2014 | Bromberg et al. |
| 2014/0243207 | A1 | 8/2014 | Takayasu |
| 2014/0332203 | A1 | 11/2014 | Meinke et al. |
| 2015/0080922 | A1 | 3/2015 | Meinke et al. |
| 2015/0123760 | A1 | 5/2015 | Meinke |
| 2015/0137920 | A1 | 5/2015 | Stelzer et al. |
| 2015/0318102 | A1 | 11/2015 | Meinke et al. |
| 2015/0336821 | A1 | 11/2015 | Meinke et al. |
| 2016/0086724 | A1 | 3/2016 | Meinke et al. |

OTHER PUBLICATIONS

C. Kleffner, et al., "Commissioning of the Carbon Beam Gantry At the Heidelberg Ion Therapy (HIT) Accelerator," *Proceedings of EPAC08* (Genoa, Italy) pp. 1842-1844 (2008).

S. A. Ishmael, et al., "Actively-Shielded, Bent Gantry System for Ion Beam Therapy Based on Round YBCO Wire," *Applied Superconductivity Conference* (2016) (1 page).

Y. Iwata, et al., "Development of a superconducting rotating-gantry for heavy-ion therapy," *Nuclear Instruments and Methods in Physics Research B*, vol. 317, pp. 793-797 (2013).

Y. Iwata et al., "Design of a superconducting rotating gantry for heavy-ion therapy," *Physical Review Special Topics—Accelerators and Beams*, vol. 15, pp. 044701-1 to 044701-14 (2012).

H. Soltner, et al., "Magnetic-Field Calculations of the Superconducting Dipole Magnets for the High-Energy Storage Ring at Fair," *Proceedings of PAC07* (Albuquerque, New Mexico) pp. 194-196 (2007).

C. Goodzeit, et al., "Combined Function Magnets Using Double-Helix Coils," *Proceedings of PAC07* (Albuquerque, New Mexico) pp. 560-562 (2007).

D.S. Robin, et al., "Superconducting toroidal combined-function magnet for a compaction beam cancer therapy gantry," *Nuclear Instruments and Methods in Physics Research A*, vol. 659, pp. 484-493 (2011).

L. Bromberg, et al., "Novel lightweight achromatic superconducting magnets for gantries," available at http://indico.psi.ch/contributionDisplay.py?sessionId=1&contribId=19&confId=3575 (2015) (25 pages).

Thibault Elhaut, et al., "Optimal Preliminary Design of Superconducting Bending Magnets With Active Shielding Using Topology Optimization Method," *IEEE Transactions on Applied Superconductivity*, vol. 22, No. 3 (2012) (5 pages).

Bernard Gastineau, et al., "Comparison Between Active and Passive Shielding Designs for a Large Acceptance Superconducting Dipole Magnet," *IEEE Transactions on Applied Superconductivity*, vol. 16, No. 2, pp. 483-488 (2006).

C. Priano, et al., "A Superconducting Magnet for a Beam Delivery System for Carbon Ion Cancer Therapy," *IEEE Transactions on Applied Superconductivity*, vol. 12, No. 1, pp. 988-992 (2002).

Y. Iwata, et.al., "Development of Curved Combined-Function Superconducting Magnets for a Heavy-Ion Rotating-Gantry," *IEEE Transactions on Applied Superconductivity*, vol. 24, No. 3 (2014) (5 pages).

S. Caspi, et al, "Progress in the Design of a Curved Superconducting Dipole for a Therapy Gantry," *Proceedings of IPAC2012* (New Orleans, Louisiana) pp. 4097-4099 (2012).

Emmanuele Ravaioli, "CLIQ: a new quench protection technology for superconducting magnets," Ph.D. thesis, University of Twente, The Netherlands (2015) (229 pages).

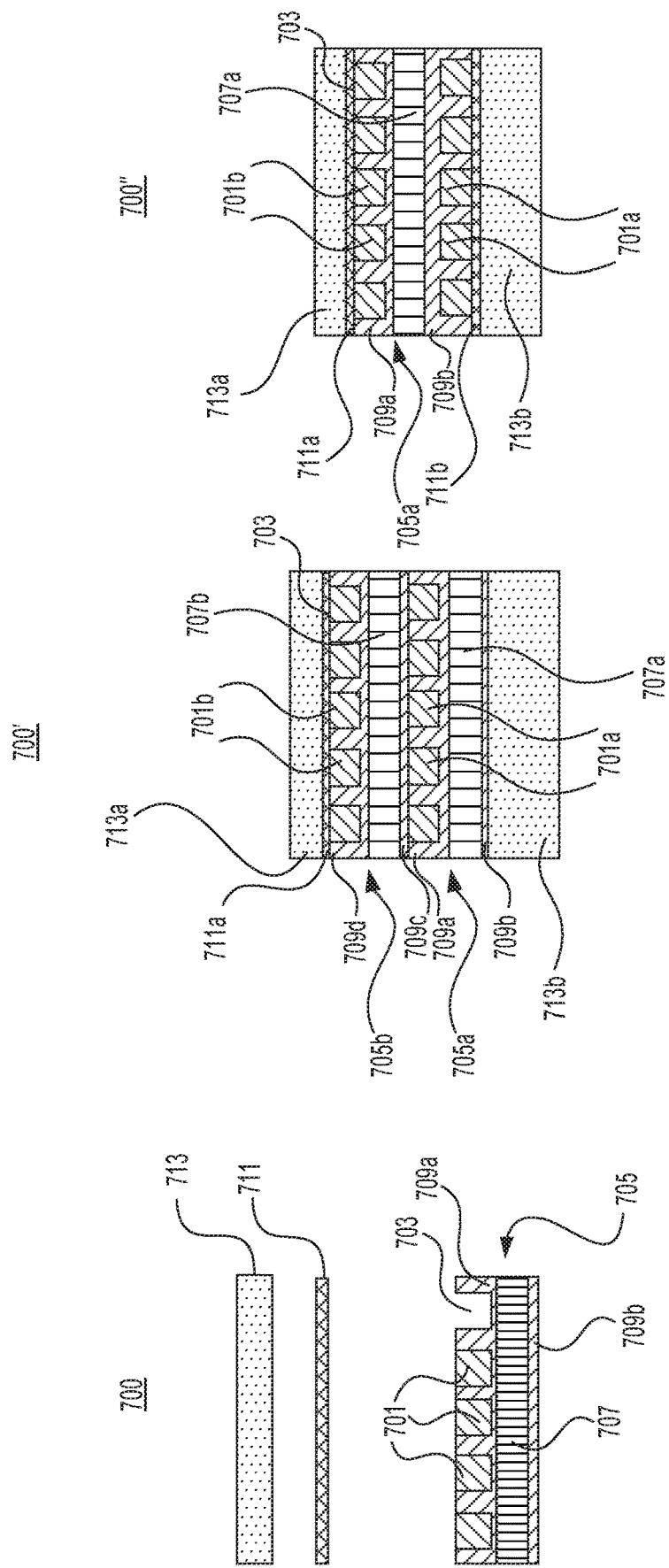

IRONLESS, ACTIVELY-SHIELDED, VARIABLE FIELD MAGNET FOR MEDICAL GANTRIES

CROSS-REFERENCE TO RELATED PATENT APPLICATIONS

This application claims the benefit of International Application No. PCT/US2016/062312, filed Nov. 16, 2016, which PCT International Application claims the benefit of priority of U.S. Provisional Patent Application No. 62/256,006, filed Nov. 16, 2015, each of which is hereby incorporated by reference in each of their entireties.

FIELD OF THE DISCLOSURE

The present disclosure relates to medical gantries, and more particularly, to superconducting magnets used in medical gantries.

BACKGROUND

Heavy ion radiotherapy is generally administered using a particle accelerator and a beam delivery system. The beam delivery system often contains a medical gantry, which combines the bending magnets and the focusing magnets for the particle beam in a single assembly. In order to significantly decrease the weight and/or size of the gantry (often by an order of magnitude), the use of superconducting magnets has been proposed. Such superconducting medical gantries use iron yokes, which serve both to amplify the magnetic field in the bore of the magnet and to shield the vicinity from the magnetic field. Shielding is also important to protect patients (particularly those with pacemakers and other electronic implants), as well as to minimize interference with nearby electronic sensors or other components near the gantry or near the patient.

However, the use of iron destroys the linearity of the magnetic field, e.g., the magnetic field would no longer increase linearly with current, such as in the high field range. The use of iron also introduces magnetic hysteresis and eddy currents in the iron, which further complicate effective treatment. For example, the magnetic field may need to be changed during the treatment procedure, and this can be more difficult due to hysteresis effects and eddy currents in the iron. Thus, it is desirable to develop medical gantries which mitigate these downsides.

Ironless medical gantries can restore the linearity lost in medical gantries containing iron yokes. Ironless medical gantries can also reduce the weight of the gantry compared with medical gantries containing iron yokes. However, ironless gantries can require significantly more current than gantries containing iron yokes. Ironless gantries can also be limited to generating a dipole field moment and are more sensitive to the size and shape of the associated particle beam. As a result, ironless gantries can also complicate effective treatment.

Thus, it may be desirable to develop new superconducting medical gantries that are ironless, yet that do not necessarily suffer from the above-noted possible drawbacks with conventional ironless gantries. The systems and methods disclosed herein may mitigate or eliminate one or more of such drawbacks.

SUMMARY

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

According to a first aspect, a superconducting magnet for an ironless medical gantry system may include a first set of coils and a second set of coils. According to some aspects, the first set of coils may be configured to generate a first magnetic field in a first region of interest and may be configured to generate a second magnetic field in a second region of interest. According to a further aspect, the second set of coils may be configured to generate a third magnetic field in the first region of interest, such that the first and third magnetic fields combine to form the target magnetic field, and may be configured to generate a fourth magnetic field in the second region of interest, such that the second and fourth magnetic fields combine to form a magnetic field smaller than the target magnetic field.

According to another aspect, a method for manufacturing a superconducting magnet for a medical gantry system may include assembling a first layer of glass fabric soaked with epoxy atop a structural shell, forming conductor grooves in the first exposed layer, winding the first conductor into the grooves, sandwiching a first layer of Litz wire between glass fabric, assembling the first sandwich above the first wound conductor, vacuum pressure impregnating the first sandwich with epoxy, forming conductor grooves in the second exposed layer, winding the second conductor into the grooves, assembling a third layer of glass fabric soaked with epoxy atop the second wound conductor, and clamping the resultant structure between the lower structural shell and an upper structural shell. According to some aspects, the first layer of glass fabric may include a second sandwich of Litz wire between glass fabric.

Exemplary objects and advantages will be set forth in part in the description which follows, or may be learned by practice of the exemplary embodiments. It is to be understood that both the foregoing general description and the following detailed description are exemplary and explanatory only and are not restrictive of the invention, as claimed.

BRIEF DESCRIPTION OF DRAWINGS

The accompanying drawings, which constitute a part of this specification, illustrate several embodiments and, together with the description, serve to explain the disclosed principles.

FIG. 7a is a schematic representation of the layers of an exemplary assembly, according to some embodiments of the present disclosure.

FIG. 7b is a schematic representation of an exemplary assembly including the layers depicted in FIG. 7a, according to some embodiments of the present disclosure.

FIG. 7c is a schematic representation of another exemplary assembly including the layers depicted in FIG. 7a, according to some embodiments of the present disclosure.

DETAILED DESCRIPTION

Figure 1:
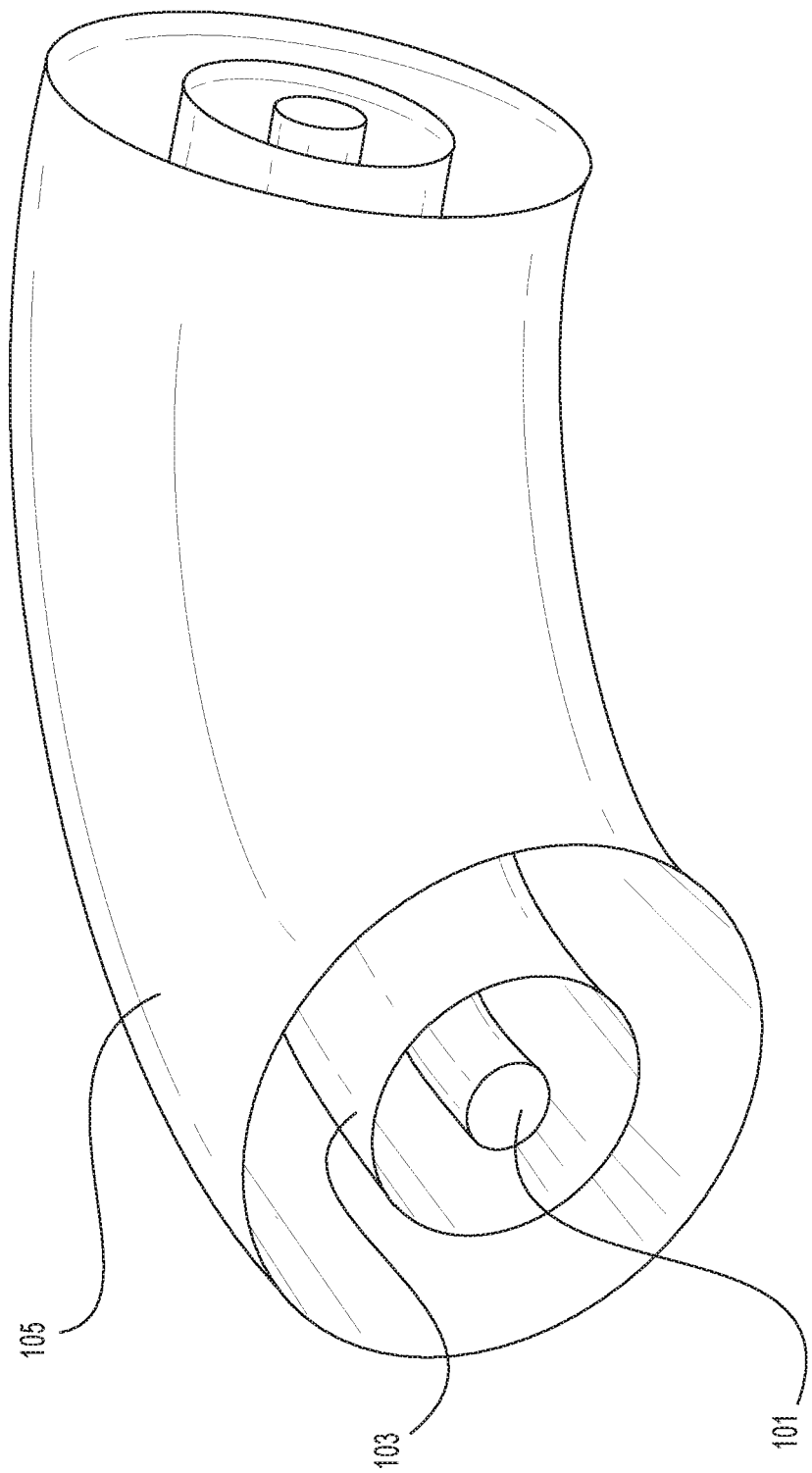
FIG. 1 is a schematic representation of the topology of an exemplary bent, actively-shielded magnet, according to some embodiments of the present disclosure.

The present disclosure generally relates to a medical gantry system. As known in the art, a medical gantry system may deliver a charged particle beam (e.g., composed of protons or ions) for particle therapy that treats cancerous tumors. A beam transport system may guide the beam from the beam's source (e.g., a particle accelerator) to the treatment room, where the beam is delivered towards the patient. As known in the art, the beam transport system include magnets for bending and/or focusing the beam as it is transported to the treatment room for delivery. Also, this beam transport system generally has an "on" cycle while a patient is undergoing treatment (during which the magnetic field is generated and the beam is bent, focused, and/or corrected), as well as an "off" cycle (during which the magnetic field and the beam are not generated and the beam transport system generally returns to room temperature). As known in the art, the beam transport system may go between the "on" and "off" cycles in accordance with various types of treatment plans for treating patients.

An example of such a medical gantry system is disclosed in U.S. Nonprovisional patent application Ser. No. 13/502,946, filed on Apr. 19, 2012, the entire disclosures of which is incorporated by reference. The present disclosure relates, more particularly, to magnets that may be used within a beam transport system of such medical gantry systems.

Magnets consistent with the present disclosure may be used within an "ironless" medical gantry system. As used herein, the term "ironless" magnets generally refers to magnets having substantially no iron or that use other means (other than iron) to cancel the stray field outside the gantry.

According to some embodiments, a magnet for an ironless medical gantry system may include a set of main coils and a set of shielding coils located around the main coils. The main coils may be configured to generate a magnetic field inside the coils. The shielding coils may also be configured to generate a magnetic field inside the coils that combines with the magnetic field generated by the main coils, forming a first overall magnetic field inside the coils. The shielding coils may also be configured to generate a magnetic field outside the coils that is used to cancel or minimize any stray magnetic field generated by the main coils outside the main coils.

In some example embodiments, an ironless magnet system may retain the benefits of traditional iron-shielded magnets, yet still remain linear. For example, as described in detail below, hysteresis may be reduced by replacing the iron of a traditional magnet with a non-ferromagnetic material. Because the hysteresis is reduced, the magnet system does not retain a magnetization after turning off the current supplied to the magnet. This, as a result, allows for easier treatment planning because there is no need to demagnetize the magnet system between treatments.

The disclosed magnet system may, according to some embodiments, be particularly lightweight. For example, the system may weigh less than 75 kilograms. For magnet systems generating higher magnetic fields, the system may weigh less than 250 kilograms. Traditional iron-shielded magnets, on the other hand, may weigh over 1900 kilograms. As a result, the cost of the ironless magnet system may be less than traditional iron-shielded magnets. At the same time, the ironless magnet system may also produce maximum magnetic field strengths of at least 2.0 Teslas. Traditional iron-shielded magnets, on the other hand, may produce maximum magnetic field strengths of no more than 2.0 Teslas. As a result, the efficiency of an ironless magnet system according to the present disclosure may be higher than traditional iron-shielded medical gantries.

According to some embodiments, the main coils may include at least one cosine-theta magnet. For example, the cosine-theta magnet may combine dipole, quadrupole, and other multipole windings in a single magnet. As a result, bending, focusing, and correction functions may be combined in the same magnet space. The shielding coils may also include at least one cosine-theta magnet. As described above, the cosine-theta magnet may combine dipole, quadrupole, and other multipole windings in a single magnet. As a result, bending, focusing, and correction functions may be combined in the same magnet space.

According to some embodiments, the main coils may include at least one double-helix magnet. For example, the double-helix magnet may combine dipole, quadrupole, and other multipole windings in a single magnet. As a result, bending, focusing, and correction functions may be combined in the same magnet space. The shielding coils may include at least one cosine-theta magnet in combination with the main coils, including at least one double-helix magnet.

The shielding coils may also include at least one double-helix magnet. As described above, the double-helix magnet may combine dipole, quadrupole, and other multipole windings in a single magnet. As a result, bending, focusing, and correction functions may be combined in the same magnet space. The main coils may include at least one cosine-theta magnet in combination with the shielding coils including at least one double-helix magnet.

FIG. 1 is a schematic representation of the general topology of bent, actively-shielded magnet 100. Magnet 100 may be used within a medical gantry system (not shown) consistent with the present disclosure. As known in the art, magnet 100 may be included as part of a beam transport system for transporting the beam from the source to a treatment room. As also known in the art, the beam transport system may control the energy or magnetic field of magnet 100 by controlling the current supplied to magnet 100.

FIG. 1 illustrates that magnet 100 may include a beam space 101 (corresponding to the transported beam), a main coil 103, and a shielding coil 105. As depicted in FIG. 1, beam space 101 may be arranged toroidally. Main coil 103 may be arranged around beam space 101, and shielding coil 105 may be arranged around main coil 103. In other embodiments, beam space 101, main coil 103, and shielding coil 105 may be substantially straight, rather than bent.

As depicted in FIG. 1, main coil 103 may be adapted to generate a first magnetic field inside the coil and to generate a second magnetic field outside the coil. Shielding coil 105 may be adapted to generate a third magnetic field inside the coil and to generate a fourth magnetic field outside the coil. The first and third magnetic fields may combine to form the overall or target magnetic field inside the coils. This target magnetic field may be used to direct the beam within beam space 101. The second and fourth magnetic fields outside the coils may combine to reduce any magnetic field outside the coils. For example, the shielding coil may generate a magnetic field that cancels or reduces any magnetic field generated by the main coil outside the main coil. While the magnetic field outside the coils is ideally close to zero, this magnetic field is preferably at least less than 500 Gauss at a distance of 2 m from the coils.

As depicted in FIG. 1, a beam (not shown) from a particle accelerator (not shown) enters beam space 101. The beam is directed along the direction of beam space 101 by the target magnetic field generated in beam space 101 by main coil 103 and shielding coil 105. The beam is thereby bent, focused, and/or corrected as required by a predetermined treatment plan and/or treatment system.

As described above, main coil 103 and shielding coil 105 may be connected to a current supply (not shown) that provides current to energize the coils and, in turn, generate the magnetic fields. Because of the advantages of ironless magnet systems consistent with the present disclosure, the current supplied to coils 103 and 105 may vary during an "on" cycle of the beam delivery system. The varying current may thus allow the magnetic field generated in beam space 101 to, in turn, also vary during a treatment "on" cycle. This variability is possible because ironless magnet systems consistent with the present disclosure enable the current within coils 103 and 105 to scale linearly with the magnetic field generated in beam space 101. Ironless magnet systems consistent with the present disclosure thus make it possible to adopt treatment plans that require or allow for adjustment of the magnetic field in beam space 101 during the treatment cycle. For example, in some embodiments, main coil 103 and shielding coil 105 may be connected in series. As a result, the current supplied to both main coil 103 and shielding coil 105 would be adjusted or varied at the same time, resulting in a proportional change to the generated magnetic fields by each of coils 103, 105.

In some embodiments, main coil 103 and shielding coil 105 may be adapted to produce a dipole moment. As known in the art, a dipole moment may bend the beam within beam space 101. In other embodiments, main coil 103 and shielding coil 105 may be adapted to produce a quadrupole moment. As known in the art, a quadrupole moment may focus the beam within beam space 101. In other embodiments, main coil 103 and shielding coil 105 may be adapted to produce higher order multipole moments. As known in the art, higher order multipole moments may correct the beam within beam space 101 (e.g., adjust the beam by small angles to correct for errors from bending and focusing). In other embodiments, main coil 103 and shielding coil 105 may be adapted to combine dipole, quadrupole, and/or other higher order multipole moments. This combination may allow bending, focusing, and/or correction functions to be combined in the same magnet space.

In some embodiments, main coil 103 and shielding coil 105 may be adapted for use with a small aperture. A small aperture magnet is a magnet wherein the main coil has a radius smaller than 8 cm, preferably between 2 cm and 6 cm, for example, 4 cm. A small aperture may allow for downstream scanning, where the beam is scanned after passing through magnet 100. In other embodiments, main coil 103 and shielding coil 105 may be adapted for use with a wide aperture. A wide aperture magnet is a magnet wherein the main coil has a radius larger than 8 cm, preferably between 15 cm and 30 cm, for example, 23 cm. A wide aperture may allow for upstream scanning, where the beam is scanned prior to passing through magnet 100.

According to some embodiments, main coil 103 and shielding coil 105 may be implemented with either a double-helix magnet or a cosine-theta magnet. While cosine-theta magnets and double-helix magnets are generally known to those of ordinary skill in the art, these magnets are also described in further detail below.

Figure 2:
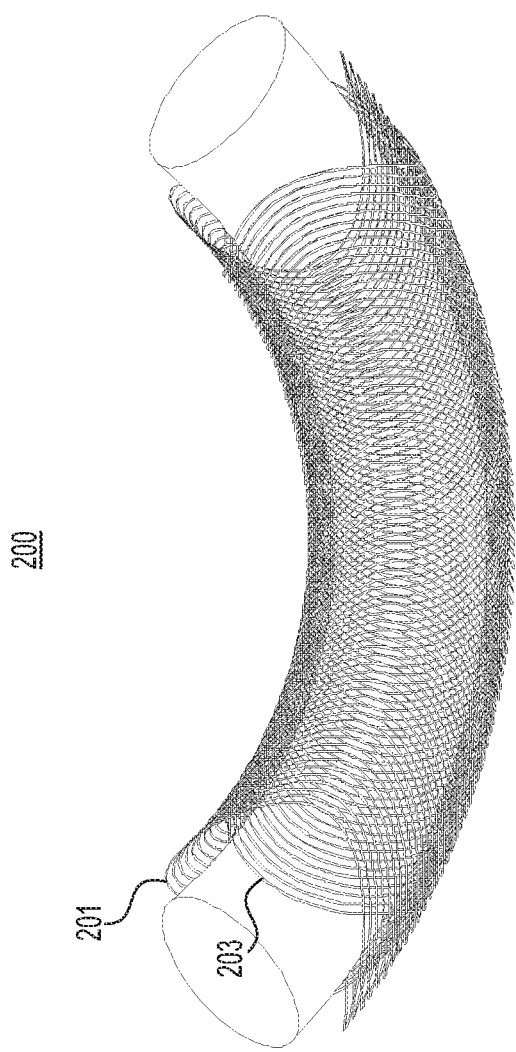
FIG. 2 is a schematic representation of the topology of a bent, double-helix magnet.

FIG. 2 is a schematic representation of the general topology of bent, double-helix magnet 200 as known to those of ordinary skill in the art. As depicted in FIG. 2a, double-helix magnet 200 may include a first layer 201 and a second layer 203. First layer 201 may be half-wound with positive tilt and half-wound with opposite tilt with respect to the mid-plane of magnet 200. Similarly, second layer 203 may be half-wound with positive tilt and half-wound with opposite tilt with respect to the mid-plane of magnet 200. The winding of first layer 201 may be the opposite of the winding of second layer 203.

Figure 3:
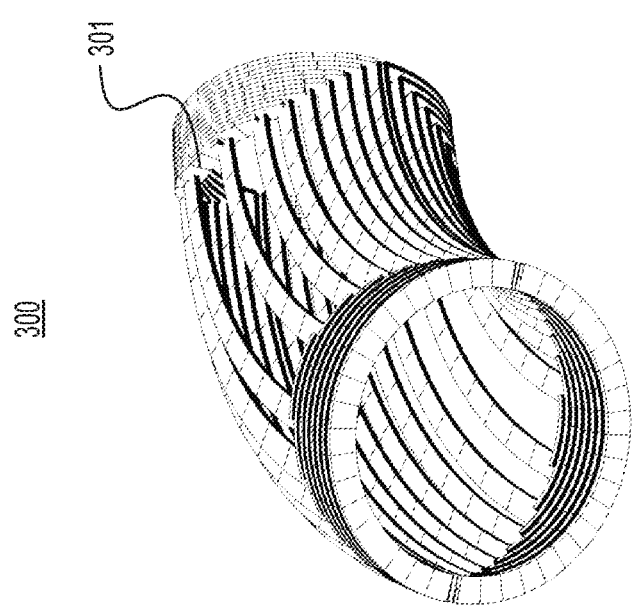
FIG. 3 is a schematic representation of the topology of a bent, cosine-theta magnet.

FIG. 3 is a schematic representation of the topology of bent, cosine-theta magnet 300 as known to those of ordinary skill in the art. As depicted in FIG. 3, cosine-theta magnet 300 may include a plurality of bent "racetracks," e.g., racetrack 301. As known in the art, the racetracks illustrated in FIG. 3 correspond to the arrangement or path of a coil or winding of magnet 300. While the racetracks shown in FIG. 3 are bent (e.g., each is curved as it extends from one linear end of magnet 300 to the other end of magnet 300), other embodiments of cosine-theta magnet 300 may be substantially straight and thus have straight racetracks.

Figure 4:
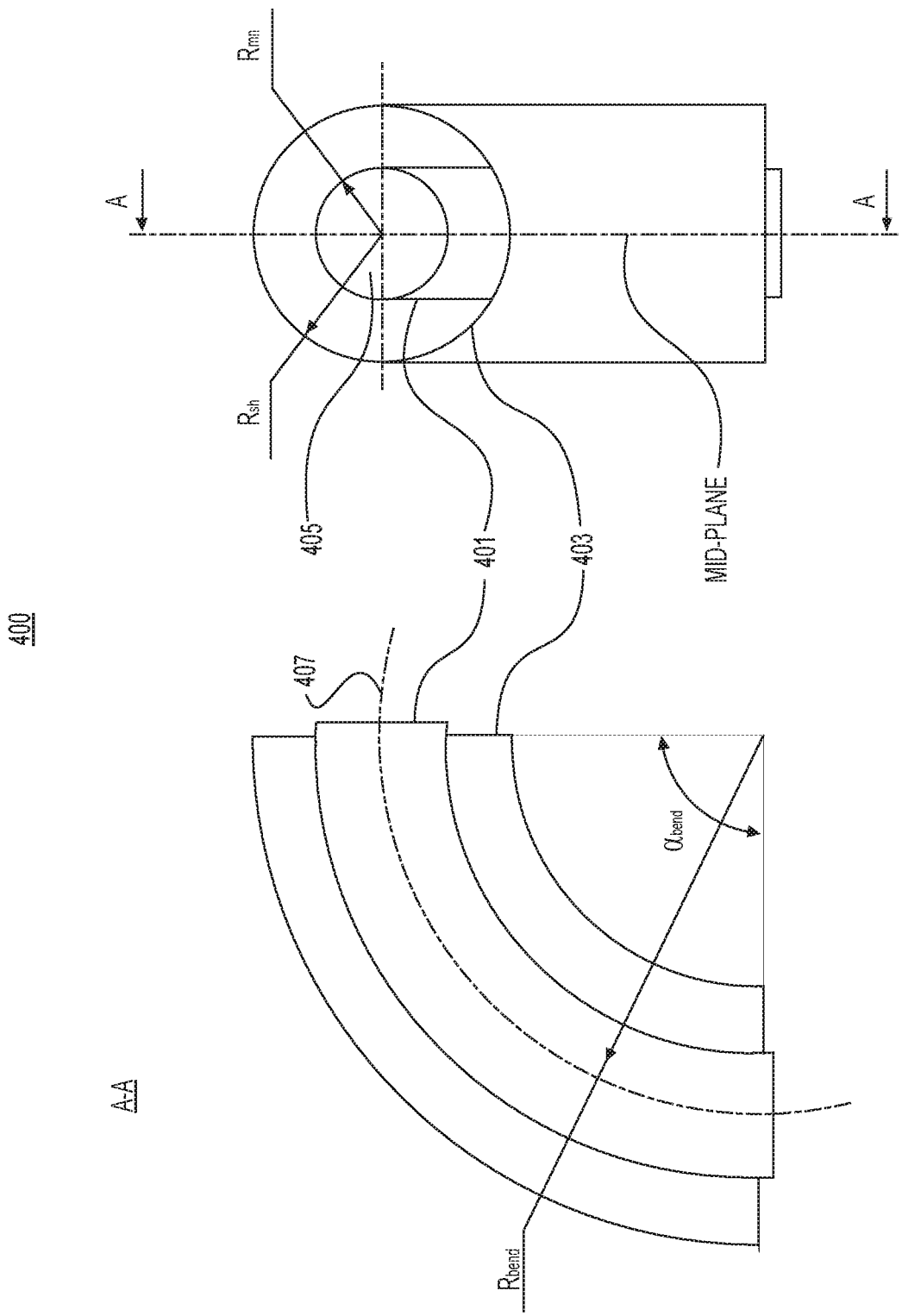
FIG. 4 is a schematic representation of an exemplary magnet system, according to some embodiments of the present disclosure.

FIG. 4 is a schematic representation of exemplary bending magnet system 400. As depicted in FIG. 4, bending radius $R_{bend}$ may define the circumferential center line of beam space 405, and bending angle $\alpha_{bend}$ may define the angle of beam space 405. Beam space 405 is the portion of the inner region of main coil 401 through which particles will traverse. Similarly, radius $r_{mn}$ may define the average radius of main coil 401, and radius $r_{sh}$ may define the average radius of shielding coil 403. In other embodiments, main coil 401 and shielding coil 403 may be straight, such that $R_{bend}$ correspondingly approaches infinity.

As depicted in FIG. 4, beam 407 enters beam space 405 and is bent along bending angle $\alpha_{bend}$ by the target magnetic field generated in beam space 405 by main coil 401 and shielding coil 403. Beam 407 may thereby be bent, focused, and/or corrected as required by a predetermined treatment plan. In some embodiments, shielding coil 403 may include fewer total ampere-turns than main coil 401. As a result, the third and fourth magnetic fields generated by coil 403 may thus be smaller than the first and second magnetic fields generated by coil 401. In some embodiments, $r_{sh}$ may be larger, smaller, or comparable to the outer dimension of a comparable, iron shielded, magnet. Increasing the size reduces the magnitude of the third magnetic fields generated by shielding coil 403 in beam space 405.

The ends of main coil 401 and shielding coil 403 may be formed as in conventional iron-shielded magnets, e.g., with constant minor radius. In such embodiments, the turns and the ends of coil 401 and coil 403 are in the same surface, which is toroidal if coil 401 and coil 403 are bent and is cylindrical if coil 401 and coil 403 are straight. In other embodiments, the ends of main coil 401 and shielding coil 403 may have a minor radius that differs from the minor radius of the turns of coil 401 and coil 403. This flexibility regarding the minor radius of the ends is useful for adjusting the field profile in the end region, and in particular, for increasing the magnetic field gradient in these regions, which minimizes the magnetic field in the regions immediately upstream and downstream from the magnet (upstream and downstream refer to the regions where the beam approaches and leaves the magnet, respectively). Alternatively, an additional set of coils (not shown) may be placed in the entrance and exit regions of system 400. These additional coils may be short compared to main coil 401 and shielding coil 403 and may generate a magnetic field in beam space 405 opposite to the first magnetic field generated by mail coil 401.

Table 1 below shows results for an example of the disclosed actively-shielded, cosine-theta magnet. In the example of Table 1, the radius of the main coil is 0.17 meters, and the radius of the shielding coil is 0.35 meters. The minor radius of the shielding coil was set to be the same as the radius of a conventional iron-shielded magnet with the same performance.

TABLE 1

| Parameter | Coil | Units | |
|---|---|---|---|
| Current | inner coil | MA-turns | 2.43 |
| | outer coil | MA-turns | 1.43 |
| Max field | inner coil | T | 2.8 |
| | outer coil | | 1.8 |
| SC weight | inner coil | kg | 42 |
| | outer coil | | 29 |
| Total SC weight | | kg | 71 |
| Magnetic energy | | kJ | 422 |
| Field at magnet boundary | | T | 0.14 |

As may be seen in Table 1, an exemplary actively-shielded, cosine-theta magnet as disclosed herein may generate a larger magnetic field inside the coils and a smaller stray magnetic field outside the coils, as compared with some traditional iron-shielded, cosine-theta magnets. As a result, an exemplary actively-shielded, cosine-theta magnet as disclosed herein may be more efficient relative to its weight and may be safer as compared with some traditional iron-shielded, cosine-theta magnets.

Table 2 below shows results for an example of the disclosed actively-shielded, double-helix magnet.

TABLE 2

| Parameter | Coil | Winding | Units | |
|---|---|---|---|---|
| Current | inner double-helix | inner helix | MA-turns | 2.68 |
| | | outer helix | MA-turns | 2.31 |
| | outer double-helix | inner helix | MA-turns | 0.73 |
| | | outer helix | MA-turns | 0.66 |
| Max field | inner double-helix | | T | 2.4 |
| | outer double-helix | | | 1.5 |
| SC weight | inner double-helix | | kg | 46 |
| | outer double-helix | | | 19 |
| Total SC weight | | | kg | 66 |
| Magnetic energy | | | kJ | 223 |
| Field at magnet boundary | | | T | 0.14 |

As may be seen in Table 2, an exemplary actively-shielded, double-helix magnet as disclosed herein may generate a larger magnetic field inside the coils and a smaller stray magnetic field outside the coils, as compared with some traditional iron-shielded, double-helix magnets. As a result, an exemplary actively-shielded, double-helix magnet as disclosed herein may be more efficient relative to its weight and may be safer as compared with some traditional iron-shielded, double-helix magnets.

Figures 5A, 5B:
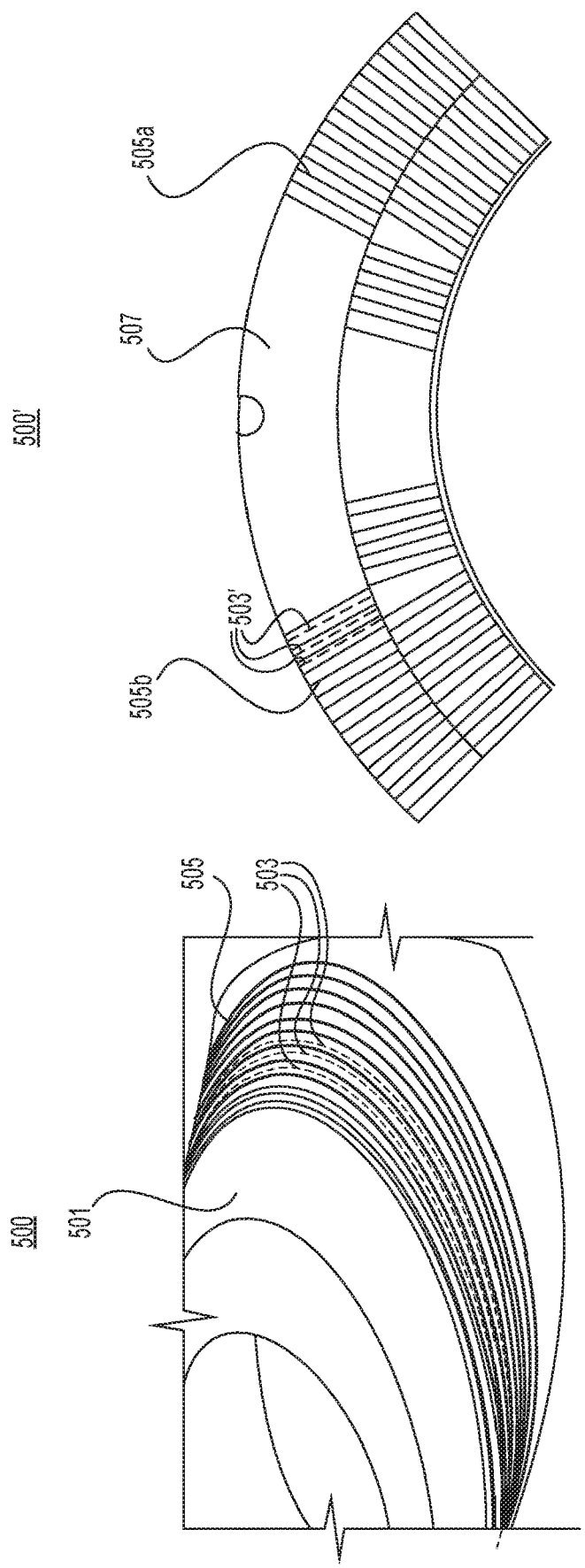
FIG. 5a is a schematic representation of a bent, double-helix magnet including a superconducting cable.
FIG. 5b is a schematic representation of a bent, cosine-theta magnet including a superconducting cable.

FIG. 5a is a schematic representation of bent, double-helix magnet 500. As depicted in FIG. 5a, magnet 500 may include a superconducting cable 503. Superconducting cable 503 generates a magnet field when current is passed through it and may generate a large magnetic field without overheating due to its superconductivity. The magnetic field generated by cable 503 may be determined by the pattern in which cable 503 is wound around the mandrel (not shown) of magnet 500. Cable 503 may be connected to a current supply (not shown) for generating a magnetic field. In some embodiments, superconducting cable 503 may include niobium-titanium, niobium-tin, magnesium diboride, YBCO, or any other superconducting material.

As further depicted in FIG. 5a, magnet 500 may include a mandrel 501 including a groove pattern 505, and superconducting cable 503 may sit inside groove pattern 505. In some embodiments, groove pattern 505 may be formed by use of a grooving machine or other appropriate machine for forming grooves. In some embodiments, superconducting cable 503 may be restrained in groove pattern 505 by toroidal structural shells (not shown), as known in the art. The shells may provide support for superconducting cable 503 against various forces, such as winding Lorentz forces, that may cause unwanted movement of cable 503 during operation.

As depicted in FIG. 5a, superconducting cable 503 generates a magnetic field when current is passed through it. Thus, mandrel 501 and superconducting cable 503 together form a superconducting magnetic coil.

FIG. 5b is a schematic representation of bent, cosine-theta magnet 500'. As depicted in FIG. 5b, magnet 500' may include superconducting cable 503'. In some embodiments, superconducting cable 503' may include niobium-titanium, niobium-tin, magnesium diboride, YBCO, or any other superconducting material. Superconducting cable 503' generates a magnetic field when current is passed through it. Thus, mandrel 501' and superconducting cable 503' may comprise a superconducting magnetic coil.

As further depicted in FIG. 5b, magnet 500' may include mandrel 501' including racetrack patterns, e.g., patterns 505a and 505b, separated azimuthally by spacers, e.g., spacer 507. In example embodiments, spacer 507 is formed of a ductile metal, e.g., bronze. Superconducting cable 503' may sit inside racetrack patterns 505a and 505b. Other embodiments may include a plurality of spacers azimuthally separating a plurality of racetrack patterns. In some embodiments, superconducting cable 503' may be restrained in racetrack patterns 505a and 505b by toroidal structural shells (not shown). The shells may provide support for superconducting cable 503' against winding Lorentz forces.

Figure 6:
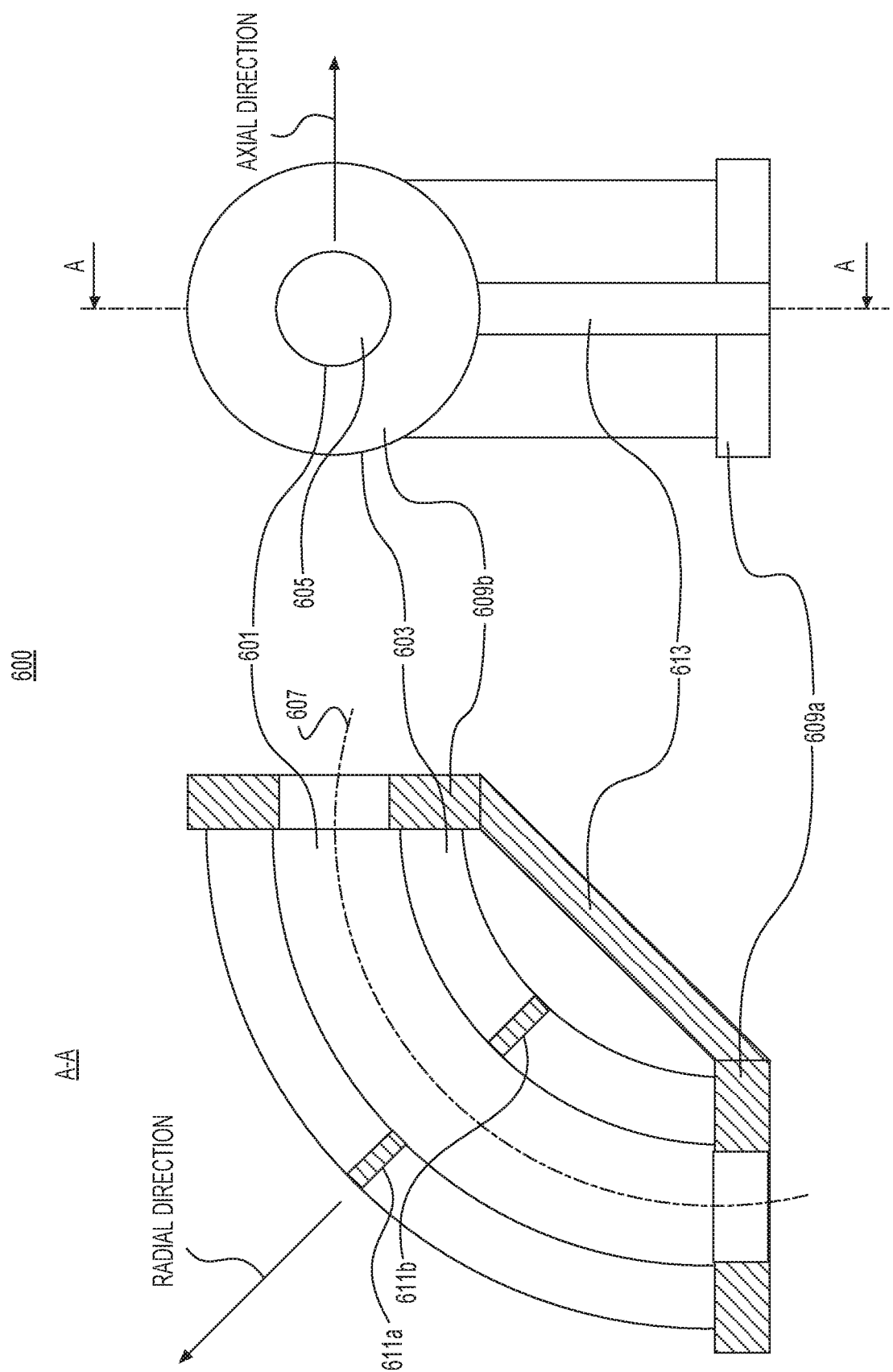
FIG. 6 is a schematic representation of an exemplary structural layout, according to some embodiments of the present disclosure.

FIG. 6 is a schematic representation of exemplary structural layout 600. As depicted in FIG. 6, shielding coil 603 may toroidally surround main coil 601. As explained above, both coils may be subject to significant Lorentz forces. For example, forces internal to each coil may tend to straighten each coil from a toroid into a straight cylinder. Similarly, forces of interaction between the coils may tend to generate destabilizing forces in both axial and radial directions. Both the axial and radial directions are labeled in FIG. 6.

As further depicted in FIG. 6, a plurality of end flanges, e.g., flanges 609a and 609b, may tie together or connect the ends of shielding coil 603 and main coil 601. The plurality of flanges may restrain shielding coil 603 and main coil 601 against the Lorentz forces described above. A plurality of radial spacers, e.g., spacers 611a and 611b, may be located at a plurality of locations along the circumference of shielding coil 603 and main coil 601. The plurality of radial spacers may limit radial and axial elastic displacements of shielding coil 603 and main coil 601. Truss plate 613 may tie flanges 609a and 609b together. Truss plate 613 may prevent forces internal to each coil from tending to straighten each coil.

In some embodiments, a plurality of ties, trusses, and/or hoops (not shown) may be located in the region between shielding coil 603 and main coil 601. The ties, trusses, and/or hoops may tie together shielding coil 603 and main coil 601. Thus, the rigidity of layout 600 may be increased, which further helps to prevent forces internal to each coil from tending to straighten each coil.

As depicted in FIG. 6, beam 607 enters beam space 605 and is bent along the labeled direction by the target magnetic field generated in beam space 605 by main coil 601 and shielding coil 603. Beam 607 is thereby bent and focused as required by a predetermined treatment plan.

In some embodiments, the medical gantry may rotate the beam around an axis. In such embodiments, the at least two sets of coils may rotate with the medical gantry about its axis. However, many convenient and passive cooling options, for example, helium baths and thermal siphoning, may not be compatible with such embodiments. In certain aspects, cooling by helium flow in cooling channels may be possible but may also require significant supervision and expensive maintenance. Conduction cooling by cryocoolers may require less supervision and cost than cooling by helium flow in cooling channels.

Additional cooling systems may be included in the magnet system in order to increase the heat capacity of the superconducting magnet. The A/C losses within the magnet system are generated during a short treatment period when the beam energy and magnetic field are both ramped. An increased heat capacity may minimize the temperature excursion experienced by the superconductor during these treatment cycles. In some embodiments, the heat capacity may be increased by placing helium conduits within the coils. Helium conduits may comprise tubing, piping, or other known ways to include internally constrained helium within the system. Preferably, the cross-sectional area of the helium conduits is less than 15% of the cross-sectional area of the coils.

FIG. 7a is a schematic representation of the layers of exemplary magnet assembly 700 adapted for the use of cryocoolers (not shown). Assembly 700 may contain a layer of conductor, e.g., conductor 701 in a plurality of grooves, e.g., groove 703. The plurality of grooves may be embedded within a G10 matrix 705. G10 matrix 705 may contain embedded Litz wire layer 707 located between layers 709a and 709b.

In the context of this disclosure, Litz wire generally refers to a range of electrically insulated segmented, stranded, or braided high conductivity materials known in the art that are used to conduct heat from the superconducting windings to a cold head, a thermal reservoir, or other cooling source. Preferably, Litz wire 707 may be formed from individual, electrically insulated strands or tapes of highly conducting material, e.g., copper or aluminum. Even more preferably, the dimension of the strands or tapes in Litz wire 707 may be adapted such that the induced eddy current losses in Litz wire 707 are small compared to the A/C losses in conductor 701.

Litz wire layer 707 may provide a good heat path between locations of the plurality of cryocoolers (not shown) and the plurality of distributed heat deposition sources (not shown), which may be spread over assembly 700. Preferably, Litz wire 707 may be directed in a direction perpendicular to the winding direction of conductor 701. Litz wire layer 707 may also result in an anisotropic thermal conduction with high thermal conductivity in the direction of Litz wire layer 707.

In some embodiments, helium conduits (not shown) may be located in the grooves, e.g., groove 703. In such embodiments, the helium conduits are located near conductor 701. In other embodiments, helium conduits (not shown) may be located in G10 matrix 705. In such embodiments, the helium conduits are located near Litz wire layer 707. The helium conduits may contain high pressure gaseous helium at room temperature that will condense when assembly 700 is lowered to cryogenic temperatures. The helium conduits are sealed in order to prevent the contained helium from escaping.

As shown in FIG. 7, Litz wire layer 707 may be sandwiched between layers of glass fabric, e.g., layers 709a and 709b. Electrical insulation 711 may insulate Litz wire layer 707 from additional Litz wire layers (not shown) in assembly 700. Insulation 711 may serve as a ground between the conductors, e.g., conductor 701, and the structural shells, e.g., 713.

G10 matrix 705 may contain epoxy filling (not shown) for holding wire layer 707 in place. The epoxy filling may prevent significant eddy currents without impeding heat conduction along Litz wire layer 707.

As depicted in FIG. 7a, conductor 701 generates a magnetic field when current is passed through it. In systems consistent with the present disclosure, conductor 701 may correspond to the main coil (e.g., coil 103 of FIG. 1) or to the shielding coil (e.g., coil 105 of FIG. 1). Conductor 701 is kept in a superconducting state using cryocoolers (not shown) and distributed heat deposition sources (not shown). The cryocoolers and heat deposition sources remove heat from conductor 701 through Litz wire layer 707. As known in the art, helium conduits (not shown) may also absorb heat from conductor 701 during treatment. Shell 713 contains the Lorentz forces acting on assembly 700 when conductor 701 generates a magnetic field.

FIG. 7b is a schematic representation of exemplary assembly 700' including the layers depicted in FIG. 7a. As depicted in FIG. 7b, assembly 700' may include structural shells 713a and 713b. Shells 713a and 713b may contain Lorentz forces developed in the conductors. In some embodiments, shells 713a and 713b may be formed of steel. In certain aspects, shells 713a and 713b may be formed of stainless steel.

As depicted in FIG. 7b, assembly 700' may include at least two layers of conductor, e.g., conductors 701a and 701b. Each layer of conductor may reside in a plurality of grooves, e.g., groove 703. Electrical insulation 711a may reside atop conductor 701b and below shell 713a. Assembly 700' may also include at least two Litz wire layers, e.g., layers 707a and 707b. In some embodiments, layer 707a may be aligned in a direction different from that of Litz wire 707b. As a result, the isotropy of assembly 700' may be increased.

As further depicted in FIG. 7b, Litz wire layer 707a may be sandwiched between layers of glass fabric, e.g., layers 709a and 709b. The sandwich including Litz wire layer 707a and glass fabric layers 709a and 709b may include epoxy filling (not shown) to form G10 matrix 705a. Similarly, Litz wire layer 707b may be sandwiched between layers of glass fabric, e.g., layers 709c and 709d. The sandwich including Litz wire layer 707b and glass fabric layers 709c and 709d may include epoxy filling (not shown) to form G10 matrix 705b.

As depicted in FIG. 7b, conductors 701a and 701b generate a magnetic field when current is passed through them. In systems consistent with the present disclosure, conductors 701a and 701b may together correspond to the main coil (e.g., coil 103 of FIG. 1) or to the shielding coil (e.g., coil 105 of FIG. 1). Conductors 701a and 701b are kept in a superconducting state using cryocoolers (not shown) and distributed heat deposition sources (not shown). The cryocoolers and heat deposition sources remove heat from conductors 701a and 701b through Litz wire layers 707a and 707b. Helium conduits (not shown) may also absorb heat from conductor 701 during treatment. Shells 713a and 713b contain the Lorentz forces acting on assembly 700' when conductors 701a and 701b generate a magnetic field.

FIG. 7c is a schematic representation of an additional exemplary assembly 700" including the layers depicted in FIG. 7a. As depicted in FIG. 7c, assembly 700" may include structural shells 713a and 713b. Shells 713a and 713b may contain Lorentz forces developed in the conductors. In some embodiments, shells 713a and 713b may be formed of steel. In certain aspects, shells 713a and 713b may be formed of stainless steel.

As depicted in FIG. 7c, assembly 700" includes one Litz wire layer 707a. Litz wire layer 707a may be sandwiched between layers of glass fabric, e.g., layers 709a and 709b. Electrical insulation 711a may reside atop conductor 701b and below shell 713a. Similarly, electrical insulation 711b may reside atop shell 713b and below conductor 701a.

Conductors 701a and 701b generate a magnetic field when current is passed through them. Conductors 701a and 701b may be kept in a superconducting state by using cryocoolers (not shown) and distributed heat deposition sources (not shown). The cryocoolers and heat deposition sources may remove heat from conductors 701a and 701b through Litz wire layer 707a. Helium conduits (not shown) may also absorb heat from conductor 701 during treatment. Shells 713a and 713b may contain the Lorentz forces acting on assembly 700" when conductors 701a and 701b generate a magnetic field. In some embodiments, assembly 700" may permit more effective cooling conditions as compared with assembly 700'. In other embodiments, assembly 700' may permit more effective cooling conditions as compared with assembly 700".

Figure 8A:
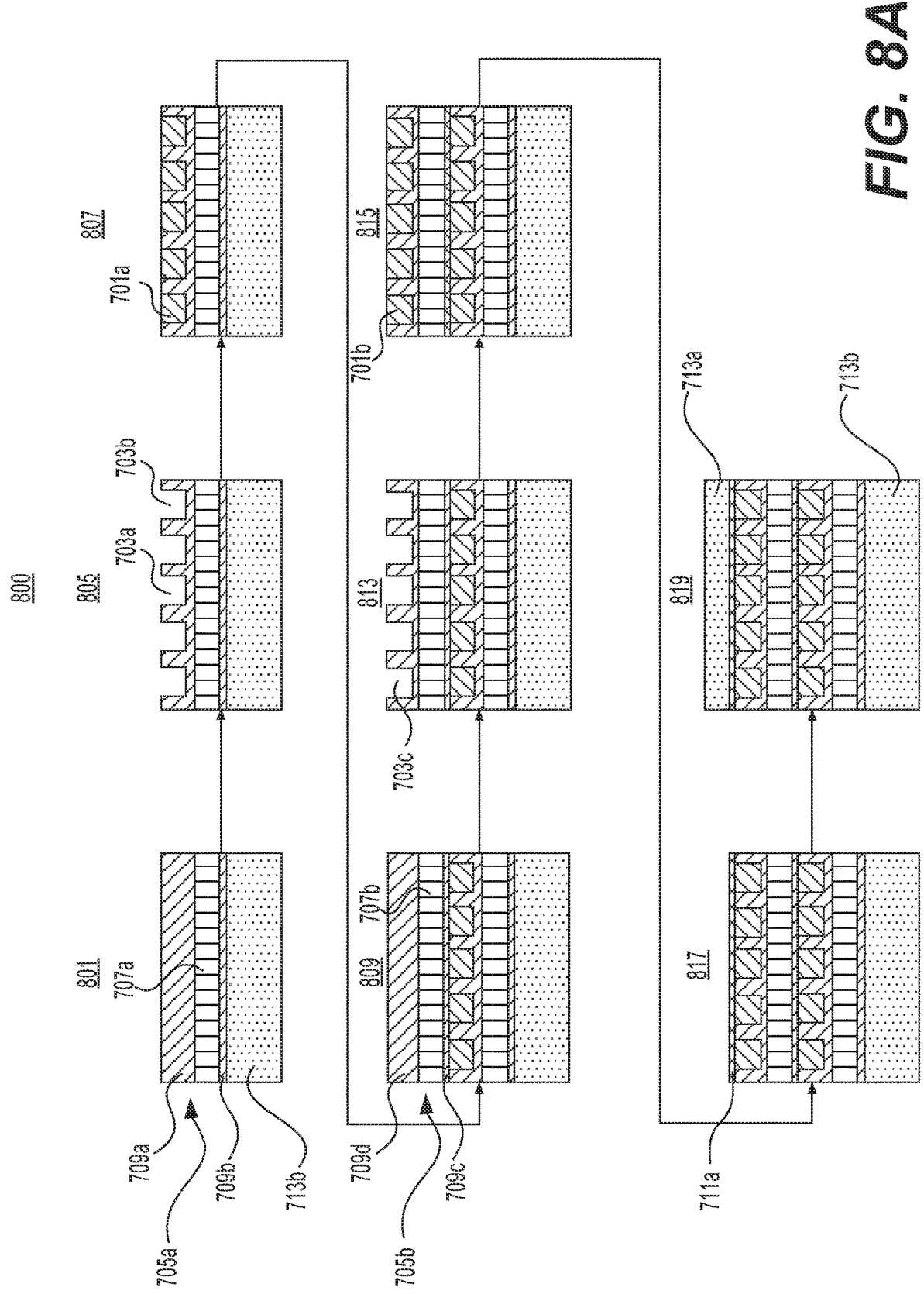
FIG. 8a is a flowchart of an exemplary method of manufacturing the assembly depicted in FIG. 7b, according to some embodiments of the present disclosure.

FIG. 8a is a flowchart of exemplary method 800 of manufacturing assembly 700'. Method 800 uses the embodiments of assembly 700' in reference to FIGS. 7a and 7b. At step 801, Litz wire layer 707a is sandwiched between layers of glass fabric, e.g., layers 709a and 709b. For example, the sandwich may be assembled atop shell 713b. In some instances, Litz wire layer 707a may be formed of copper or aluminum. At step 803 (not shown), the sandwich including Litz wire layer 707a and glass fabric layers 709a and 709b is vacuum pressure impregnated with epoxy (not shown) and is heat treated to form G10 matrix 705a. For example, G10 matrix 705a may be characterized as a solid with embedded Litz wire layer 707a.

At step 805, a plurality of grooves, e.g., 703a and 703b, are machined in the exposed layer of G10 matrix 705a. At step 807, conductor 701a is wound into the plurality of grooves, e.g., 703a and 703b, atop G10 matrix 705a. FIG. 8a depicts the top half of the assembly 700'. Assembly 700' is cylindrical or toroidal such that structural shell 713b surrounds a beam space. Conductor 701a is wound around the axis of the cylindrical or toroidal shape of assembly 700'.

At step 809, Litz wire layer 707b is sandwiched between layers of glass fabric, e.g., layers 709c and 709d. For example, Litz wire layer 707b may be formed of copper or aluminum. In some instances, the sandwich including Litz wire layer 707b and glass fabric layers 709c and 709d may be assembled atop the layer including conductor 701a. At step 811 (not shown), the sandwich including Litz wire layer 707b and glass fabric layers 709c and 709d is vacuum pressure impregnated with epoxy (not shown) and is heat treated to form G10 matrix 705b. For example, G10 matrix 705b may be characterized as a solid with embedded Litz wire layer 707b.

At step 813, a plurality of grooves, e.g., 703c, are machined in the exposed layer of G10 matrix 705b. At step 815, conductor 701b is wound into the plurality of grooves, e.g., 703c and 703d, atop G10 matrix 705b. FIG. 8a depicts the top half of the assembly 700'. Assembly 700' is cylindrical or toroidal such that structural shell 713b surrounds a beam space. Conductor 701b is wound around the axis of the cylindrical or toroidal shape of assembly 700'. At step 817, electrical insulation 711a is assembled atop the layer including conductor 701b. In some instances, electrical insulation 711a may be wet wound atop the layer including conductor 701b. In other instances, electrical insulation 711a may be dry wound atop the layer including conductor 701b. In some instances, electrical insulation 711a may be formed of glass fabric. In some instances, electrical insulation 711a may also include epoxy mixed with the glass fabric.

At step 819, structural shell 713a is clamped atop electrical insulation 711a. For example, shells 713a and 713b may include steel. In some instances, shells 713a and 713b may include stainless steel. In some instances, shells 713a and 713b may each be characterized as a half torus split at its mid-plane. In some instances, shells 713a and 713b may be bolted together along the inner diameter and outer diameter circumferences. For example, shells 713a and 713b may include pre-fabricated flanges with bolt holes at the mid-plane edges of the shells. In other instances, shells 713a and 713b may be welded together along the inner diameter and outer diameter circumferences. For example, shells 713a and 713b may include pre-fabricated welding preps at the mid-plane edges of the shells.

The example method 800 may include additional steps. For example, in some embodiments, method 800 may include assembling cryocoolers and heat deposition sources on assembly 800'. Method 800 may further include winding helium conduits with conductors 701a and 701b or including helium conduits with Litz wires 707a and 707b.

Further, while not shown in FIG. 8a, assembly 700' may also be heat treated. This may advantageously solidify any remaining epoxy in assembly 700'. The ends of conductors 701a and 701b may also be connected to each other at this time. Finally, the steps of method 800 may be modified in any manner, including reordering steps and/or inserting or deleting steps.

Figure 8B:
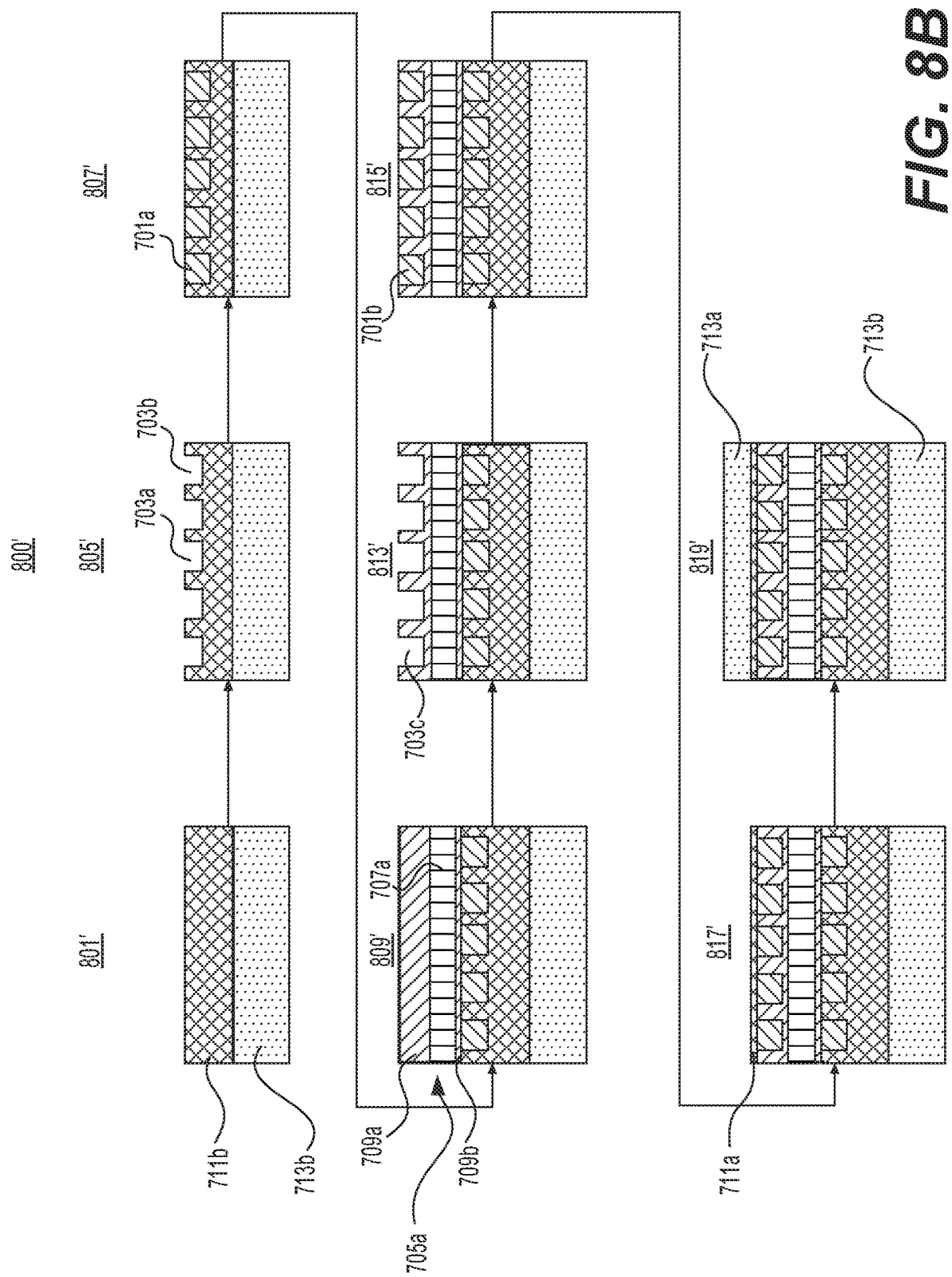
FIG. 8b is a flowchart of an exemplary method of manufacturing the assembly depicted in FIG. 7c, according to some embodiments of the present disclosure.

FIG. 8b is a flowchart of exemplary method 800' of assembly 700''. Method 800' uses the embodiments of assembly 700'' in reference to FIGS. 7a and 7c. At step 801', electrical insulation 711b is assembled atop shell 713b. In some instances, electrical insulation 711b may be formed of glass fabric. In some instances, electrical insulation 711b may also include epoxy mixed with the glass fabric. At step 803' (not shown), electrical insulation 711b may be heat treated. This may solidify the epoxy included in electrical insulation 711b. At step 805', a plurality of grooves, e.g., 703a and 703b, are machined in the exposed layer of electrical insulation 711b.

At step 807', conductor 701a may then be wound into the plurality of grooves, e.g., 703a and 703b, atop electrical insulation 711b. FIG. 8b depicts the top half of the assembly 700''. Assembly 700'' is cylindrical or toroidal such that structural shell 713b surrounds a beam space. Conductor 701a is wound around the axis of the cylindrical or toroidal shape of assembly 700''.

At step 809', Litz wire layer 707a is sandwiched between layers of glass fabric, e.g., layers 709a and 709b. For example, Litz wire layer 707a may be formed of copper or aluminum. In some instances, the sandwich including Litz wire layer 707a and glass fabric layers 709a and 709b may be assembled atop the layer including conductor 701a. At step 811' (not shown), the sandwich including Litz wire layer 707a and glass fabric layers 709a and 709b may be vacuum pressure impregnated with epoxy (not shown) and is heat treated to form G10 matrix 705a. For example, G10 matrix 705a may be characterized as a solid with embedded Litz wire layer 707a. At step 813', a plurality of grooves, e.g., 703c, are machined in the exposed layer of G10 matrix 705a.

At step 815', conductor 701b may then be wound into the plurality of grooves, e.g., 703c and 703d, atop G10 matrix 705a. At step 817', electrical insulation 711a is assembled atop the layer including conductor 701b. In some instances, electrical insulation 711a may be wet wound atop the layer including conductor 701b. In other instances, electrical insulation 711a may be dry wound atop the layer including conductor 701b. In some instances, electrical insulation 711a may include glass fabric. In some instances, electrical insulation 711a may also include epoxy.

At step 819', structural shell 713a is clamped atop electrical insulation 711a. For example, shells 713a and 713b may include steel. In some instances, shells 713a and 713b may include stainless steel. In some instances, shells 713a and 713b may each be characterized as a half torus split at its mid-plane. In some instances, shells 713a and 713b may be bolted together along the inner diameter and outer diameter circumferences. For example, shells 713a and 713b may include pre-fabricated flanges with bolt holes at the mid-plane edges of the shells. In other instances, shells 713a and 713b may be welded together along the inner diameter and outer diameter circumferences. For example, shells 713a and 713b may include pre-fabricated welding preps at the mid-plane edges of the shells.

The example method 800' may include additional steps. For example, in some embodiments, method 800' may include assembling cryocoolers and heat deposition sources on assembly 700''. Method 800' may further include winding helium conduits with conductors 701a and 701b or including helium conduits with Litz wire 707a.

Further, while not shown in FIG. 8b, assembly 700'' may also be heat treated. This may advantageously solidify any remaining epoxy in assembly 700''. The ends of conductors 701a and 701b may also be connected to each other at this time. Finally, the steps of method 800' may be modified in any manner, including reordering steps and/or inserting or deleting steps.

Figure 9:
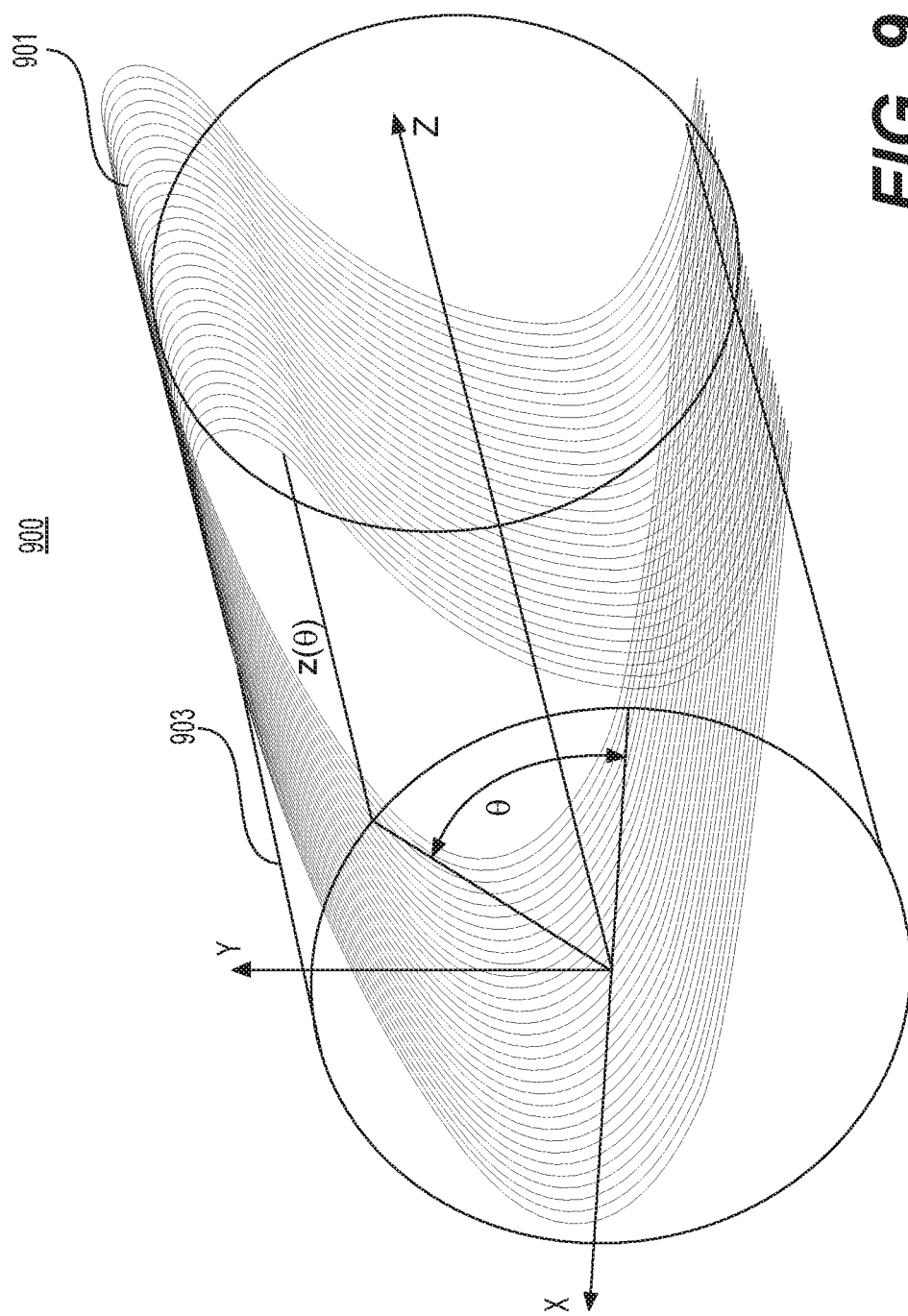
FIG. 9 is a schematic representation of a conventional double-helix magnet modulated for a quadrupolar field.

FIG. 9 is a schematic representation of traditional double-helix magnet 900 modulated for a quadrupolar field. Conductor 901 may be wound according to modulated angle θ, which may represent the angle between laid conductor 901 and the direction of cylinder 903. A second winding (not shown) may mirror wound conductor 901. The second winding may serve to cancel the solenoidal component of the magnetic field within the bore. As depicted in FIG. 9, conductor 901 generates a quadrupolar magnetic field when current is passed through it.

Figure 10B:
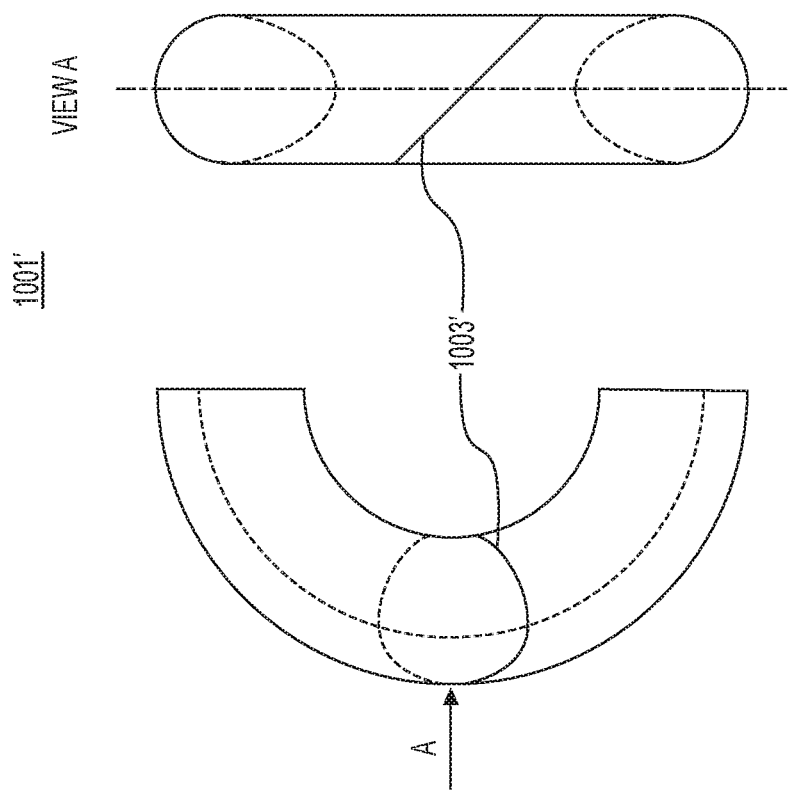
FIG. 10b is a schematic representation of a single turn of a conductor in an exemplary alternative double-helix magnet modulated for a dipole field, according to some embodiments of the present disclosure.
Figure 10A:
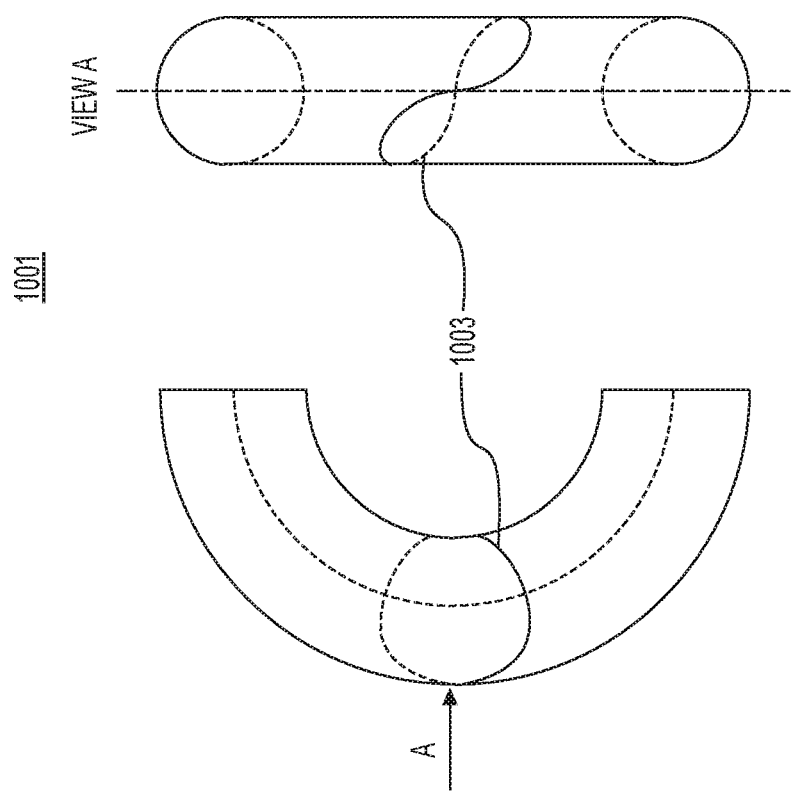
FIG. 10a is a schematic representation of a single turn of a conductor in a bent, double-helix magnet modulated for a dipole field.

FIG. 10a is a schematic representation of a conventional single turn of conductor 1003 in bent, double-helix magnet 1001 modulated for a dipole field. As depicted in FIG. 10a, a conventional modulation of double-helix winding, e.g., as depicted in FIG. 9, for use in a toroidal magnet may be rather complex. In particular, as depicted in FIG. 10a, each turn of conductor 1003 may extend across multiple plane sections of magnet 1001. As a result, the winding process may be rather inefficient, both with respect to time and to cost. A second winding (not shown) may mirror wound conductor 1003. The second winding may serve to cancel the solenoidal component of the magnetic field within the bore. As depicted in FIG. 10a, conductor 1003 generates a dipolar magnetic field when current is passed through it.

FIG. 10b is a schematic representation of a single turn of conductor 1003' in alternative double-helix magnet 1001' modulated for a dipole field. As depicted in FIG. 10b, modulation of double-helix winding, e.g., as depicted in FIG. 9, for use in a toroidal magnet may be simpler than in a conventional magnet 1001, as depicted in FIG. 10a. For example, magnet 1001' may deviate from the constant-minor-radius torus of magnet 1001. As a result, each turn of conductor 1003' may lie in a single plane section of magnet 1001'. A second winding (not shown) may mirror wound conductor 1003'. The second winding may serve to cancel the solenoidal component of the magnetic field within the bore. As depicted in FIG. 10b, conductor 1003' generates a dipolar magnetic field when current is passed through it.

Figure 11A:
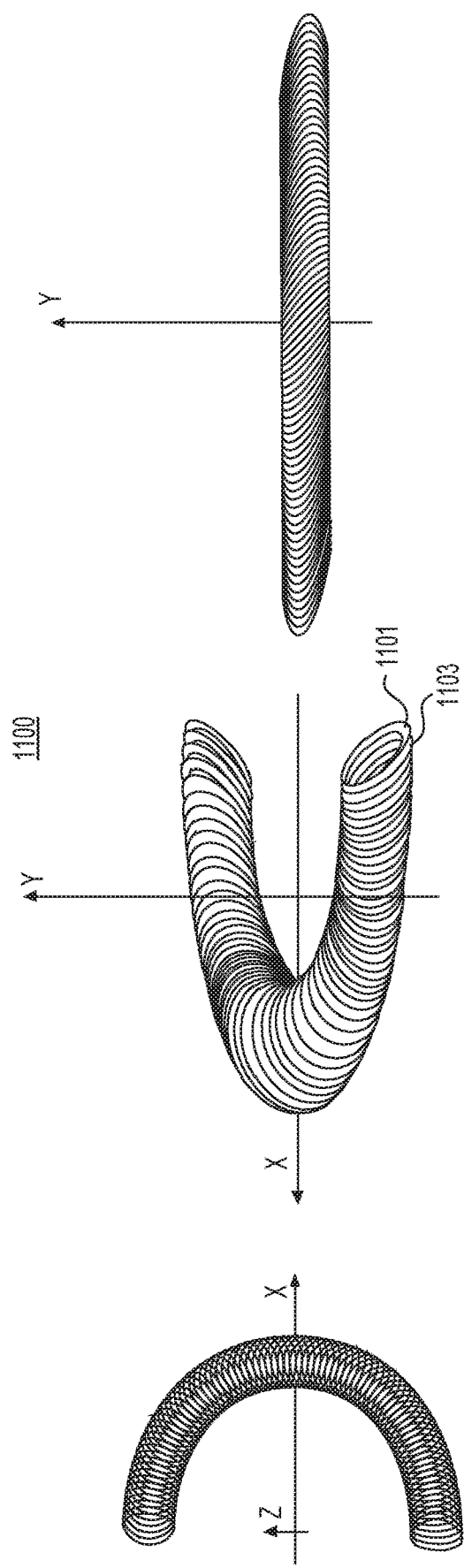
FIG. 11a is a schematic representation of an exemplary modular design of the exemplary alternative double-helix magnet depicted in FIG. 10b, according to some embodiments of the present disclosure.

FIG. 11a is a schematic representation of exemplary modular design 1100 of exemplary alternative double-helix magnet 1001' depicted in FIG. 10*b*. Advantageously, alternative double-helix magnet 1001', unlike traditional magnet 1001, may include a plurality of solenoidal modules, e.g., modules 1101 and 1103.

Figure 11B:
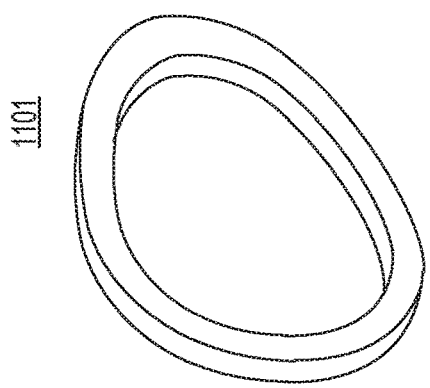
FIG. 11b is a schematic representation of a solenoidal module of the exemplary modular design depicted in FIG. 11a, according to some embodiments of the present disclosure.

FIG. 11*b* is a schematic representation of solenoidal module 1101 of exemplary modular design 1100 depicted in FIG. 11*a*. Module 1101 may be wound by a small conductor (not shown) using a multi-layered arrangement including a plurality of turns per layer. In some embodiments, magnet 1001' may be assembled from continuously wound solenoidal modules. In other embodiments, magnet 1001' may be assembled from separately wound solenoidal modules, e.g., module 1101.

Figure 12A:
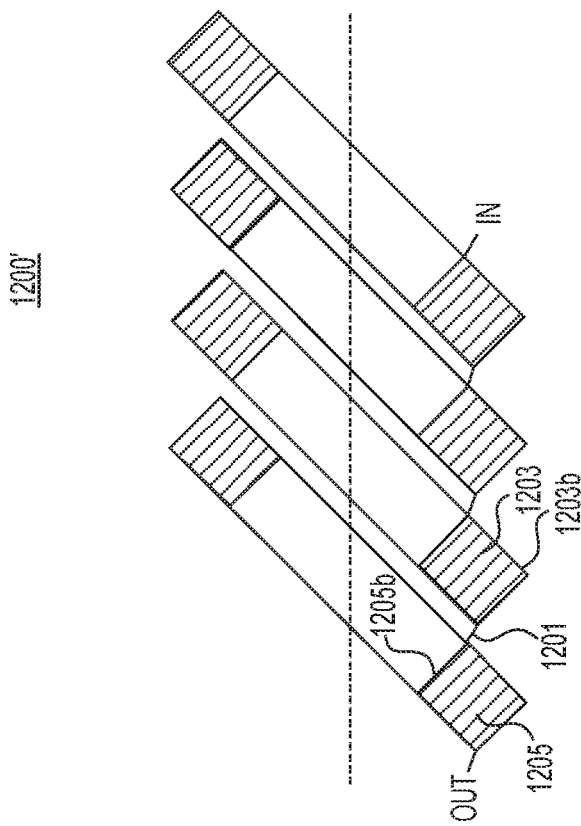
FIG. 12a is a schematic representation of an exemplary intermodular transition for the inner and outer layers of the exemplary modular design depicted in FIG. 11a, according to some embodiments of the present disclosure.

FIG. 12*a* is a schematic representation of exemplary intermodular transition 1200 for the inner and outer layers of exemplary modular design 1100 depicted in FIG. 11*a*. As depicted in FIG. 12*a*, a plurality of transitions, e.g., transition 1201, extend from the plurality of upper ends, e.g., upper end 1203*a*, of the plurality of solenoidal modules, e.g., module 1203, to the plurality of lower ends, e.g., lower end 1205*b*, of the plurality of adjacent solenoidal modules, e.g., modules 1205.

Figure 12B:
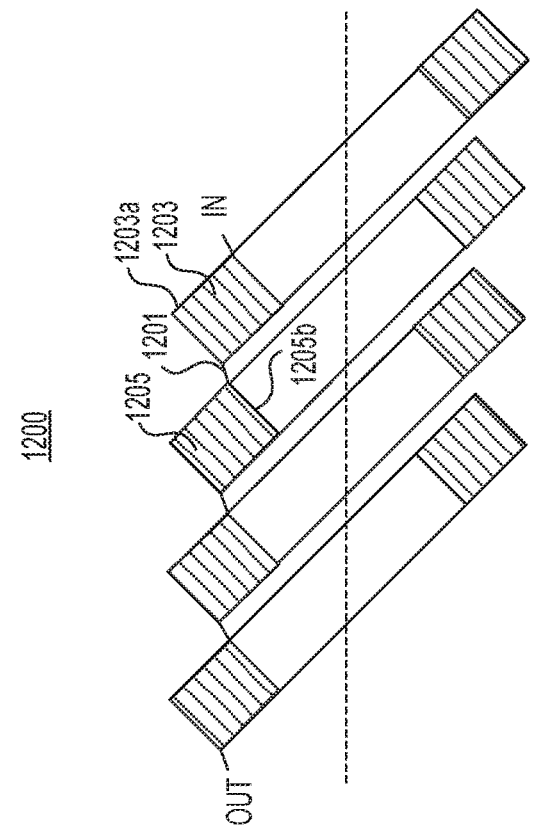
FIG. 12b is a schematic representation of another exemplary intermodular transition for the inner and outer layers of the exemplary modular design depicted in FIG. 11a, according to some embodiments of the present disclosure.

FIG. 12*b* is a schematic representation of another exemplary intermodular transition 1200' for the inner and outer layers of exemplary modular design 1100 depicted in FIG. 11*a*. As depicted in FIG. 12*b*, a plurality of transitions, e.g., transition 1201, extend from the plurality of lower ends, e.g., lower end 1203*b*, of the plurality of solenoidal modules, e.g., module 1203, to the plurality of upper ends, e.g., upper end 1205*a*, of the plurality of adjacent solenoidal modules, e.g., module 1205.

In general, most superconducting coils may include a quench protection system. Superconducting coils may experience damaging overheating when a portion of the superconducting cable becomes normally conducting. As a result, the energy stored in the magnet must be extracted safely. In traditional superconductors, the current in the superconducting cable may be rapidly discharged on an external dump resistor. However, the superconducting coils may contain a high terminal voltage. As a result, the external dump resistor may experience a short when discharging the high terminal voltage. A short in the dump resistor may present a greater danger than the overheating itself.

Alternatively, the energy stored in the magnet may be extracted using inductive quenching. For example, a quench winding may be inductively coupled with the superconducting coils. The quench winding may be adapted to carrying a high-frequency A/C current, which may induce additional A/C losses in the superconducting coils. These additional A/C losses may permit a rapid transition of the superconducting cable to a normally conducting cable. Advantageously, the rapid transition may reduce the possibility of damaging overheating. However, inductive quenching may require a significant number of quench winding within the magnet, which may increase size and cost.

Alternatively, the energy stored in the magnet may be extracted using the Coupling-Loss Induced Quench (CLIQ) technique. For example, a CLIQ circuit may include a capacitor, a floating voltage supply, and two resistive current leads. The resistive current leads may connect the circuit to the magnet, a thyristor, and a reverse diode. The leads may be adapted to carry only pulsed currents. For example, the leads may have a cross-section of a few square millimeter.

In general, the floating voltage supply may charge the capacitor. The thyristor may generate an oscillating current in the superconducting coils. The oscillating current may induce a rapid transition of the superconducting cable to a normally conducting cable. This rapid transition may reduce the possibility of damaging overheating.

However, the CLIQ technique may cause a reserve current in the main power converter if the CLIQ technique is used while the current in the superconducting coils is below a certain threshold. A reverse diode may be connected across the main power converter, which may protect the main power converter from a reverse current. The CLIQ technique may not require additional winding within the magnet, as is generally required for inductive quenching.

Figure 13:
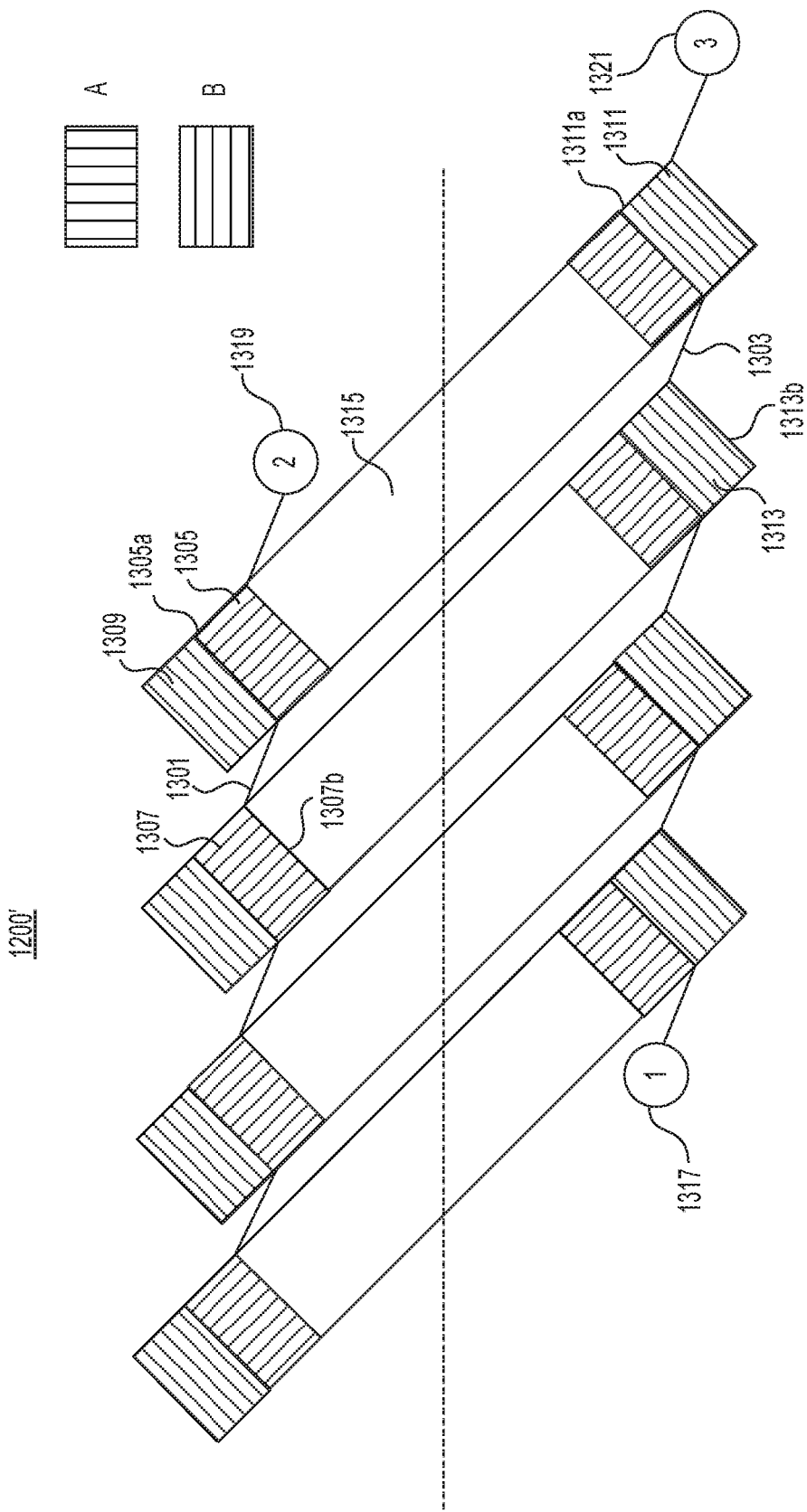
FIG. 13 is a schematic representation of an exemplary intermodular transition adapted to include CLIQ-compatible terminals, according to the present disclosure.

FIG. 13 is a schematic representation of exemplary intermodular transition 1200' adapted to include CLIQ-compatible terminals, e.g., first terminal 1315, second terminal 1317, and third terminal 1319. As depicted in FIG. 13, the plurality of solenoidal modules, e.g., module 1313, may contain a plurality of first sub-coils, e.g., sub-coil 1305, and a plurality of second sub-coils, e.g., sub-coil 1309. As further depicted in FIG. 13, a first plurality of transitions, e.g., transition 1301, may extend from the plurality of upper ends, e.g., upper end 1305*a*, of the plurality of first sub-coils, e.g., sub-coil 1305, to the plurality of lowers ends, e.g., lower end 1307*b*, of the plurality of adjacent first sub-coils, e.g., sub-coil 1307. Similarly, a second plurality of transitions, e.g., transition 1303, may extend from the plurality of upper ends, e.g., upper end 1311*a*, of the plurality of second sub-coils, e.g., sub-coil 1311, to the plurality of lowers ends, e.g., lower end 1313*b*, of the plurality of adjacent second sub-coils, e.g., sub-coil 1313.

Figure 14:
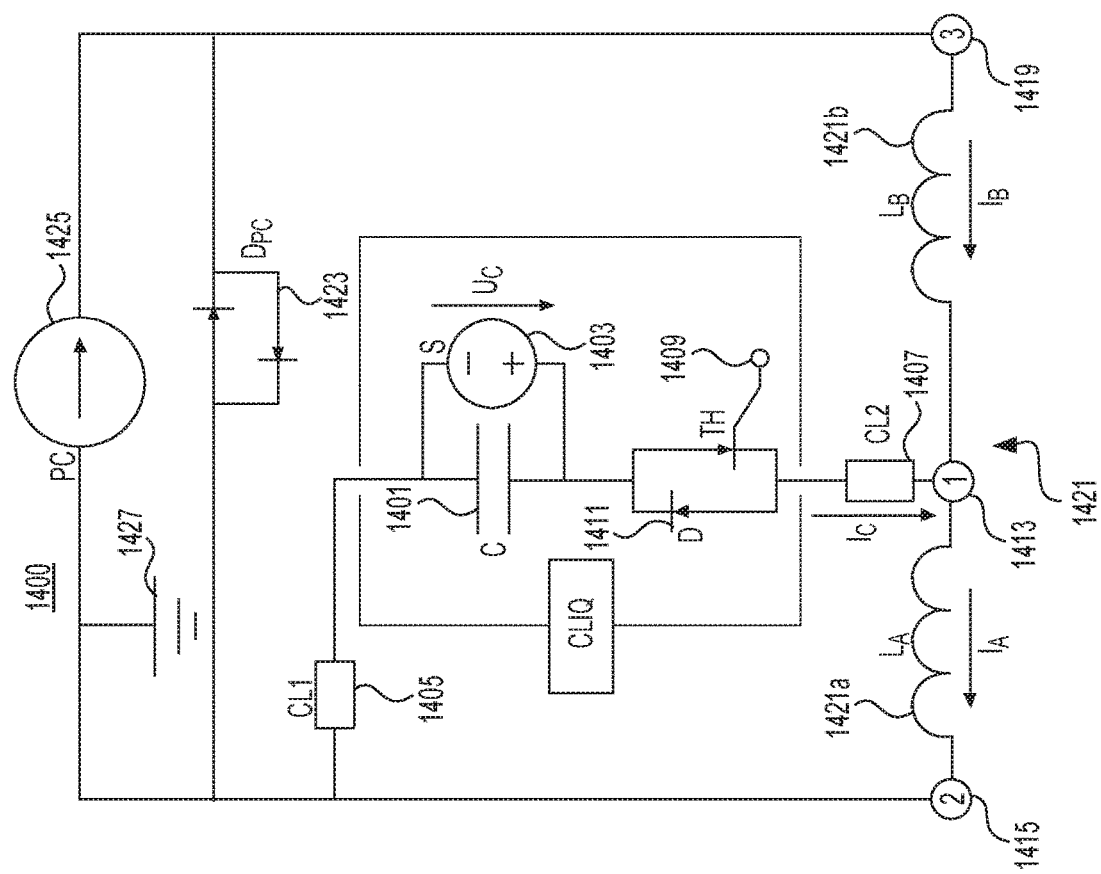
FIG. 14 is a schematic representation of a CLIQ circuit.

FIG. 14 is a schematic representation of exemplary CLIQ circuit 1400 adapted for use with exemplary intermodular transition 1200' depicted in FIG. 13. As depicted in FIG. 14, circuit 1400 may include capacitor 1401, floating voltage supply 1403, and resistive current leads 1405 and 1407. Lead 1405 may connect circuit 1400 to a first portion 1421*a* of superconducting coil 1421. Similarly, lead 1407 may connect circuit 1400 to thyristor 1409 and reverse diode 1411. In some embodiments, leads 1405 and 1407 may be adapted to carry only pulsed currents. For example, the leads may have a cross-section of a few square millimeter.

As depicted in FIG. 14, first terminal 1413 and second terminal 1415 may connect to alternate ends of first portion 1421*a* of superconducting coil 1421. Similarly, first terminal 1413 and third terminal 1417 may connect to alternate ends of second portion 1421*b* of superconducting coil 1421. Reverse diode 1423 may be connected across main power converter 1425, which may be connected to main power supply 1427. Reverse diode 1423 may protect main power converter 1425 from a reverse current when the circuit 1400 is activated.

As further depicted in FIG. 14, supply 1403 charges capacitor 1401. Thyristor 1409 may then generate an oscillating current $I_C$. Oscillating current $I_C$ partially flows in one direction through first portion 1421*a* of superconducting coil 1421 and partially flows in a second direction through second portion 1421*b* of superconducting coil 1421. Oscillating current $I_C$ induces a rapid transition of superconducting cable 1421 to a normally conducting cable.

CLIQ circuit 1400 may be optimized by minimizing the equivalent inductance $L'_{eq}$ comprised of the self-inductances, $L'_A$ and $L'_B$, of first portion 1421*a* and second portion 1421*b* of superconducting coil 1421, and the mutual inductance, $M'_{AB}$, of the magnet windings. The equivalent inductance $L'_{eq}$ may be defined as shown below in Equation 1.

$$L'_{eq} = \frac{L'_A L'_B - M'^2_{AB}}{L'_A + L'_B + M'_{AB}} \qquad \text{Equation 1}$$

Sub-coils A and B may be closely electromagnetically coupled, such that $L'_A \approx L'_B = M'_{AB}$, and $L'_{eq} \to 0$. Advantageously, this may minimize the equivalent inductance $L'_{eq}$, which may maximize efficiency of CLIQ circuit 1400.

Figure 15B:
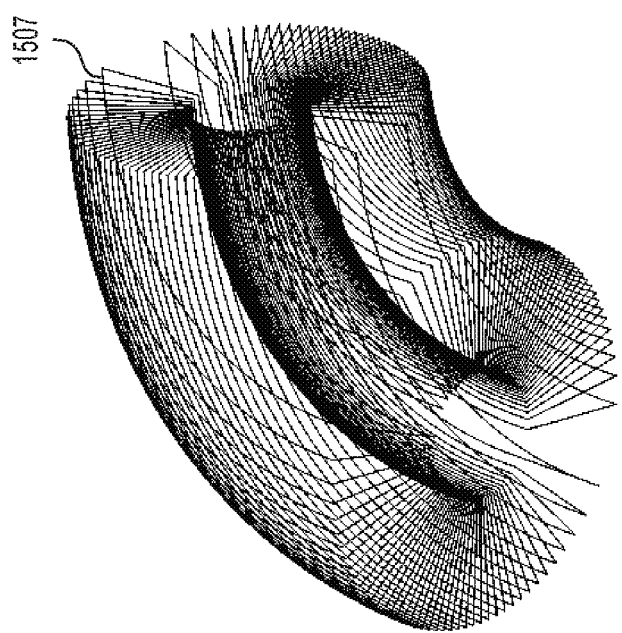
FIG. 15 is a schematic representation of an exemplary alternative cosine-theta magnet, according to some embodiments of the present disclosure.
Figure 15A:
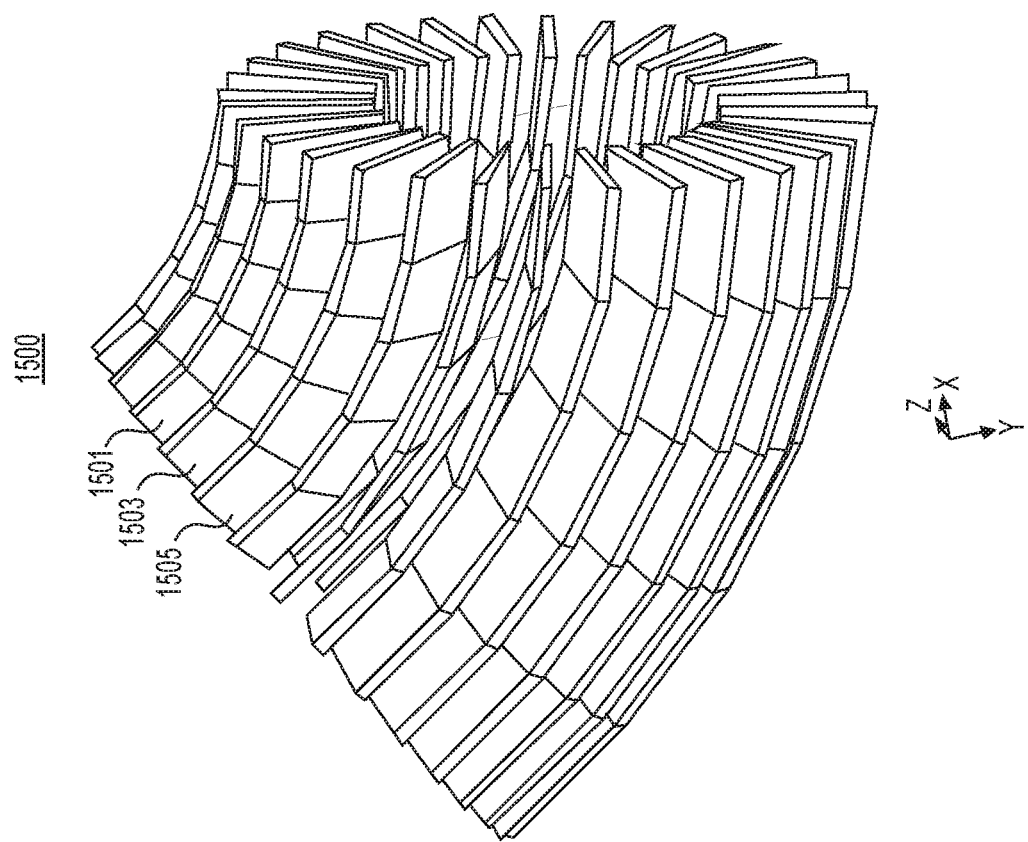

FIG. 15*a* is a schematic representation of alternative cosine-theta magnet 1500. As depicted in FIG. 15*a*, magnet 1500 may include a plurality of plates, e.g., plates 1501, 1503, and 1505. Coils 1507 (which are shown separately in FIG. 15*b*) may wrap around the plates in a deformed race-track configuration. In some embodiments, the coils may be manufactured using 3-D printing or 3-D machining. This may reduce the difficulty in winding the coils due to the non-planar nature of the plates. In some embodiments, the plates may include glass-epoxy and Litz wire. This may both permit for thermal conduction and reduce undesired electrical conduction. As shown in FIGS. 15*a* and 15*b*, the coils generate a magnetic field when current is passed through them.

Magnet 1500 may further include a inner magnet (not shown). Preferably, the inner magnet may be a small, traditional cosine-theta magnet and may reside inside the hollow of the plates of magnet 1500. Advantageously, the inner magnet may carry approximately one-third of the current of the inner magnet in a traditional double cosine-theta magnet. For example, the inner magnet may carry approximately 1 MA-turns, and the race-track coils may carry 1.43 MA-turns for a total of 2.43 MA-turns. In other embodiments, magnet 1500 may further include an outer magnet (not shown). Preferably, the outer magnet may be a traditional cosine-theta magnet and may surround the plates of magnet 1500. For example, the outer magnet may carry approximately 1 MA-turns, and the race-track coils may carry 2.43 MA-turns for a total of 2.43 MA-turns.

Other embodiments will be apparent to those skilled in the art from consideration of the specification and practice of the embodiments disclosed herein. It is intended that the specification and examples be considered as exemplary only.

What is claimed is:

1. A magnet for transporting a particle beam in a target magnet field, comprising:
   a beam entrance configured to receive the particle beam along a first direction;
   a first set of coils configured to generate a first magnetic field in a first region and to generate a second magnetic field in a second region, wherein at least the first magnetic field is configured to cause the particle beam to change direction; and
   a second set of coils configured to generate a third magnetic field in the first region and to generate a fourth magnetic field in the second region, wherein at least the third magnetic field is configured to cause the particle beam to change direction; and
   a beam exit configured to output the particle beam along a second direction, wherein the first direction and the second direction form an angle greater than 0 degrees and less than 360 degrees,
   wherein:
      the first magnetic field and the target magnetic field have a common magnetic direction,
      the second region is outside the first and second coils,
      the first and third magnetic fields combine to form the target magnetic field, and
      the second and fourth magnetic fields combine to form a field of lower amplitude than the target magnetic field.

2. The magnet of claim 1, wherein the magnet is non-ferromagnetic.

3. The magnet of claim 1, wherein the magnet is toroidal, and the first set of coils and the second set of coils are bent.

4. The magnet of claim 1, wherein the magnet is substantially straight, and the first set of coils and the second set of coils are substantially straight.

5. The magnet of claim 1, wherein at least one of the first set of coils and the second set of coils includes at least one cosine-theta magnet.

6. The magnet of claim 1, wherein at least one of the first set of coils and the second set of coils includes at least one double-helix magnet.

7. The magnet of claim 1, wherein the first set of coils includes at least one cosine-theta magnet, and the second set of coils includes at least one double-helix magnet.

8. The magnet of claim 1, further comprising:
   a first conductor located in an upstream end of the magnet between the first set of coils and the second set of coils; and
   a second conductor located in a downstream end of the magnet between the first set of coils and the second set of coils,
   wherein the first conductor is configured to modify the target magnetic field directly upstream the magnet, and the second conductor is configured to modify the target magnetic field directly downstream the magnet.

9. The magnet of claim 1, wherein the magnet is configured to generate at least a dipole moment.

10. The magnet of claim 1, wherein the magnet is configured to generate at least a quadrupole moment.

11. The magnet of claim 1, wherein the magnet is configured to generate at least a magnetic moment of higher order than a quadrupole.

12. The magnet of claim 1, wherein the magnet is adapted for use with a small aperture.

13. The magnet of claim 1, wherein the magnet is adapted for use with a wide aperture.

14. The magnet of claim 1, wherein the magnet weighs less than 250 kilograms.

15. The magnet of claim 1, wherein the first and third magnetic fields combine to form a maximum target field of at least 2.0 Teslas.

16. The magnet of claim 1, wherein the second and fourth magnetic fields combine to form a field of lower amplitude than 500 Gauss.

17. The magnet of claim 1, further comprising:
   a truss,
   wherein the truss is placed in a gap between the first set of coils and the second set of coils, and
   wherein the truss is configured to increase the strength and rigidity of the magnet.

18. The magnet of claim 1, further comprising:
   a conduit containing a thermally conductive material,
   wherein the thermally conductive material is configured to allow for conduction cooling of the magnet.

19. The magnet of claim 18, wherein the thermally conductive material comprises static helium.

20. The magnet of claim 1, wherein the current in the first set of coils changes proportionally to the current in the second set of coils.

21. The magnet of claim 1, wherein the first set of coils and the second set of coils are connected in series.

22. The magnet of claim 1, wherein the first set of coils surround a first inner space through which the particle beam passes.

23. The magnet of claim 22, wherein the second set of coils surround a second inner space through which the particle beam passes.

24. The magnet of claim 23, wherein the first inner space and the second inner space overlap, at least in part, such that the overlapping space forms a beam space through which the particle beam passes.

25. The magnet of claim 24, wherein the particle beam is directed from the beam entrance to the beam exit within the beam space.

* * * * *